(12) United States Patent
Schiavinato Eberlin et al.

(10) Patent No.: US 12,306,204 B2
(45) Date of Patent: May 20, 2025

(54) APPARATUS AND METHODS FOR CLEANING AND/OR EXCHANGING MEDICAL DEVICES

(71) Applicants: BOARD OF REGENTS, THE UNIVERSITY OF TEXAS SYSTEM, Austin, TX (US); BAYLOR COLLEGE OF MEDICINE, Houston, TX (US)

(72) Inventors: Livia Schiavinato Eberlin, Austin, TX (US); Thomas Milner, Austin, TX (US); Jialing Zhang, Austin, TX (US); Noah Giese, Austin, TX (US); John Lin, Austin, TX (US); Jeffrey R. Kuhn, Austin, TX (US); James Suliburk, Houston, TX (US); Nitesh Katta, Austin, TX (US)

(73) Assignees: BOARD OF REGENTS, THE UNIVERSITY OF TEXAS SYSTEM, Austin, TX (US); BAYLOR COLLEGE OF MEDICINE, Houston, TX (US)

( * ) Notice: Subject to any disclaimer, the term of this patent is extended or adjusted under 35 U.S.C. 154(b) by 777 days.

(21) Appl. No.: 17/383,981

(22) Filed: Jul. 23, 2021

(65) Prior Publication Data
US 2022/0196697 A1 Jun. 23, 2022

Related U.S. Application Data

(63) Continuation of application No. PCT/US2020/014749, filed on Jan. 23, 2020.
(Continued)

(51) Int. Cl.
*G01N 35/10* (2006.01)
*A61B 10/00* (2006.01)
(Continued)

(52) U.S. Cl.
CPC ..... *G01N 35/1095* (2013.01); *A61B 10/0045* (2013.01); *A61B 10/0283* (2013.01);
(Continued)

(58) Field of Classification Search
CPC ............ G01N 35/1095; A61B 10/0045; A61B 10/02; A61B 10/0283; A61B 10/04; A61B 2010/045
See application file for complete search history.

(56) References Cited

U.S. PATENT DOCUMENTS 4,221,568 A 9/1980 Boettger
4,777,363 A 10/1988 Eiceman et al.
(Continued)

FOREIGN PATENT DOCUMENTS

WO 2009109879 A2 9/2009
WO 2015061597 A1 4/2015
(Continued)

OTHER PUBLICATIONS

Extended European Search Report for Application No. 20744884.6 dated Aug. 25, 2022, 9 pages.
(Continued)

*Primary Examiner* — Jennifer Wecker
(74) *Attorney, Agent, or Firm* — Meunier Carlin & Curfman LLC

(57) ABSTRACT

Methods and apparatus are provided for cleaning or exchanging medical devices. Certain embodiments may include a cassette comprising a plurality of medical devices, where the orientation of the cassette can be changed while the cassette is coupled to a processing instrument.

14 Claims, 25 Drawing Sheets

Related U.S. Application Data

(60) Provisional application No. 62/796,834, filed on Jan. 25, 2019.

(51) Int. Cl.
    *A61B 10/02*    (2006.01)
    *A61B 10/04*    (2006.01)
    *H01J 49/04*    (2006.01)

(52) U.S. Cl.
    CPC .......... *A61B 10/04* (2013.01); *H01J 49/0413* (2013.01); *A61B 2010/045* (2013.01)

(56) References Cited

U.S. PATENT DOCUMENTS

| | | | |
|---|---|---|---|
| 5,100,402 A | 3/1992 | Fan | |
| 5,152,277 A | 10/1992 | Honda et al. | |
| 5,241,990 A | 9/1993 | Cook | |
| 5,384,260 A | 1/1995 | Osborne et al. | |
| 5,607,389 A | 3/1997 | Edwards et al. | |
| 5,711,816 A | 1/1998 | Kirlin et al. | |
| 5,742,050 A | 4/1998 | Amirav et al. | |
| 5,746,720 A | 5/1998 | Stouder, Jr. | |
| 6,066,848 A | 5/2000 | Kassel et al. | |
| 6,096,276 A * | 8/2000 | Laursen | B01J 19/0046 422/65 |
| 6,432,064 B1 | 8/2002 | Hibner et al. | |
| 6,803,566 B2 | 10/2004 | Van | |
| 6,808,510 B1 | 10/2004 | Difiore | |
| 10,643,832 B2 | 5/2020 | Eberlin et al. | |
| 2001/0042828 A1 | 11/2001 | Hindsgaul et al. | |
| 2003/0193020 A1 | 10/2003 | Van | |
| 2004/0014227 A1 | 1/2004 | Frederick et al. | |
| 2004/0059530 A1 | 3/2004 | Paulse et al. | |
| 2005/0061967 A1 | 3/2005 | Shvartsburg et al. | |
| 2005/0256424 A1 | 11/2005 | Zimmon | |
| 2006/0169030 A1 | 8/2006 | Stewart et al. | |
| 2006/0292607 A1 | 12/2006 | Caprioli | |
| 2007/0114375 A1 | 5/2007 | Pevsner et al. | |
| 2007/0135779 A1 | 6/2007 | Lalomia et al. | |
| 2007/0197954 A1 | 8/2007 | Keenan | |
| 2007/0284983 A1 | 12/2007 | Wayner | |
| 2008/0045939 A1 | 2/2008 | Lee | |
| 2008/0156985 A1 | 7/2008 | Venter et al. | |
| 2008/0217524 A1 | 9/2008 | Mawer et al. | |
| 2008/0243141 A1 | 10/2008 | Privitera et al. | |
| 2009/0039283 A1 | 2/2009 | Franzen et al. | |
| 2009/0302211 A1 | 12/2009 | Takats | |
| 2010/0148057 A1 | 6/2010 | Jarrell et al. | |
| 2010/0176287 A1 | 7/2010 | Ribbing et al. | |
| 2010/0224013 A1 | 9/2010 | Van Berkel et al. | |
| 2010/0317964 A1 | 12/2010 | Hendriks et al. | |
| 2011/0087160 A1 | 4/2011 | Temple | |
| 2011/0133077 A1 | 6/2011 | Henion et al. | |
| 2011/0198495 A1 | 8/2011 | Hiraoka | |
| 2011/0253889 A1 | 10/2011 | Ishimaru et al. | |
| 2011/0284735 A1 | 11/2011 | Van Berkel et al. | |
| 2012/0053065 A1 | 3/2012 | Van Berkel | |
| 2012/0080592 A1 | 4/2012 | Wiseman et al. | |
| 2012/0083045 A1 | 4/2012 | Van Berkel et al. | |
| 2012/0149009 A1 | 6/2012 | Levis et al. | |
| 2013/0131470 A1 | 5/2013 | Galinkin et al. | |
| 2013/0164754 A1 | 6/2013 | Malik et al. | |
| 2014/0216177 A1 | 8/2014 | Van Berkel et al. | |
| 2014/0222023 A1 | 8/2014 | Kim et al. | |
| 2014/0353488 A1 | 12/2014 | Takats | |
| 2015/0202005 A1 | 7/2015 | Fuflyigin et al. | |
| 2015/0230738 A1 | 8/2015 | Cooks et al. | |
| 2015/0299808 A1 | 10/2015 | Gonzalez Diaz et al. | |
| 2016/0008030 A1 | 1/2016 | Buster et al. | |
| 2016/0041138 A1 | 2/2016 | Pycke et al. | |
| 2016/0047831 A1 | 2/2016 | Cooks et al. | |
| 2016/0181078 A1 | 6/2016 | Kovarik | |
| 2016/0181079 A1 | 6/2016 | Berkout | |
| 2016/0296215 A1 | 10/2016 | Bouamrani et al. | |
| 2016/0314956 A1 | 10/2016 | Cooks et al. | |
| 2016/0341712 A1 | 11/2016 | Agar | |
| 2017/0014149 A1 | 1/2017 | Nakayashiki et al. | |
| 2018/0036733 A1 * | 2/2018 | Williams | B01L 3/50825 |
| 2018/0038838 A1 | 2/2018 | Karancsi et al. | |
| 2018/0059119 A1 | 3/2018 | Takáts et al. | |
| 2018/0059126 A1 | 3/2018 | Jones et al. | |
| 2018/0067097 A1 | 3/2018 | Eberlin et al. | |
| 2018/0078298 A1 | 3/2018 | Gonzalez et al. | |
| 2018/0144916 A1 | 5/2018 | Richardson et al. | |
| 2018/0158661 A1 | 6/2018 | Eberlin et al. | |
| 2018/0238776 A1 | 8/2018 | Karancsi et al. | |

FOREIGN PATENT DOCUMENTS

| | | |
|---|---|---|
| WO | 2016142689 A1 | 9/2016 |
| WO | 2018045208 A1 | 3/2018 |
| WO | 2019104328 A1 | 5/2019 |

OTHER PUBLICATIONS

International Search Report and Written Opinion mailed May 19, 2020 in International Application No. PCT/US20/14749.

Ifa, et al., "Ambient ionization mass spectrometry for cancer diagnosis and surgical margin evaluation." Clinical chemistry 62.1 (2016): 111-123.

Kauppila, TJ et al., Effect of the solvent flow rate on the ionization efficiency in atmospheric pressure photoionization-mass spectrometry. Journal of the American Society for Mass Spectrometry. 2005, 16, 1399-1407.

Zhang, J et al., Nondestructive tissue analysis for ex vivo and in vivo cancer diagnostics using a handheld mass spectrometry system. Science transnational medicine. 2017, 9(406), eean3968.

* cited by examiner

APPARATUS AND METHODS FOR CLEANING AND/OR EXCHANGING MEDICAL DEVICES

CROSS-REFERENCE TO RELATED APPLICATIONS

This application is a continuation of International Application No. PCT/US2020/014749, filed Jan. 23, 2020, which claims priority to U.S. Provisional Patent Application Ser. No. 62/796,834 filed Jan. 25, 2019, the entire contents of each of which are incorporated herein by reference.

GOVERNMENT SUPPORT

This invention was made with government support under Grant No. R00 CA190783 awarded by the National Institutes of Health. The government has certain rights in the invention.

BACKGROUND OF THE INVENTION

1. Field of the Invention

The present invention relates generally to the field of medicine, molecular biology and biochemistry. More particularly, it concerns apparatus and methods for cleaning and/or exchanging surgical devices, including for example, those used for assessment of tissue samples using mass spectrometry.

2. Description of Related Art

Currently, there is no automatic option for solving the contamination of the conduit system that couples devices to during medical procedures, including for example, probes for sample acquisition and mass spectrometers or other analysis equipment. It is important to avoid cross-contamination of samples to ensure accuracy in the analysis or diagnosis of such samples.

For example, clinical diagnosis is commonly performed through the evaluation of tissue samples pre-operatively, intra-operative, and post-operatively, at several other stages of a patient's evaluation and treatment process. In particular, tissue evaluation is important in the diagnosis and management of cancer patients. Intra-operative pathologic assessment of excised tissues, for example, is routinely performed for diagnosis and surgical margin evaluation in a variety of cancer surgeries.

Typically, the resected tissue specimens are sent to a nearby room, often called the "frozen room", for tissue preparation, staining, and evaluation. The tissue specimen is frozen, sectioned, stained, and interrogated using light microscopy by an expert pathologist who carefully evaluates if the surgical margins contain cancer cells (positive margin) or not (negative margin). While intraoperative frozen section analysis has been performed in clinical practice for decades, it presents many challenges. Freezing artifacts occur during tissue processing and interfere with tissue structure and cell morphology, thus complicating pathologic interpretation, causing the analysis to be unreliable and subjective. Moreover, certain tumor cells are very difficult to recognize due to their atypical pattern of growth and shape.

Molecular approaches could provide highly accurate and potentially real-time assessments of tissue samples. Coupling the molecular approaches with minimally invasive surgical techniques, or non-invasive techniques could provide a highly accurate, yet low trauma, way to assess and diagnose tissue and surgical samples. However, to date, adequate devices or methodologies have not been developed that provide effective molecular assessment of tissue samples. Such devices and methodologies would benefit from the ability to efficiently exchanging and/or clean the instruments used to obtain samples during the sample acquisition procedure.

SUMMARY OF THE INVENTION

Exemplary embodiments of the present disclosure include apparatus and methods for efficiently exchanging and/or cleaning instruments during surgical procedures. In a specific embodiment, an apparatus comprises a cassette with a plurality of sample acquisition probes coupled to a mass spectrometer. It is understood the scope of the present disclosure includes other embodiments with a cassette comprising other types of medical devices coupled to other types of instruments. For example, embodiments of the present disclosure can be coupled to medical instruments performing spectroscopy utilizing infrared, ultraviolet, and fluorescence analysis.

There are different ways for treating cancer, however, surgery remains the main treatment option. Diagnosing tools for guiding surgeries are very important. Currently, different groups or companies are inventing various techniques for improving diagnosis efficiency and accuracy. However, for margin evaluation, multiple sites of analysis would be needed and the cross-contamination between each analysis will potentially affect the accuracy of the analysis if there is complicated tubing exchange or washing steps needed. Therefore, there is a significant need in the operating room environment to have a system which could efficiently and rapidly provide a ready-to-use device within a short period of time (e.g. a few seconds).

Exemplary embodiments of the present disclosure include an apparatus and method for intra-surgical device exchange or washing to eliminate cross contamination between analyses. While the embodiments described herein are directed to sample acquisition systems, it is understood that the scope of the invention includes other systems for performing medical procedures. Exemplary embodiments are broadly applicable to other surgical devices prone to contamination issues that are used in the operating room, especially those that use mass spectrometry for analysis.

Exemplary embodiments of the present disclosure provide multiple ways to eliminate contamination between each sample acquisition and analysis. For example, certain embodiments can automatically exchange the medical instruments and associated conduit. Other embodiments can provide a quick washing circle to regenerate the previously used conduit. For the new conduit exchange method, there are loading cassette(s) to provide ready-to-use conduit systems. For the conduit washing method, a washing port can be coupled to the analyzing system so that it could do online washing while the other instruments and conduit are being used.

Accordingly, exemplary embodiments include an apparatus and method for automatic intra-surgical device exchange or cleaning with the goal of eliminating cross contamination between each procedure, including for example, a mass-spectrometry analytic measurement. Cross contamination or carry-over within surgical devices can be detrimental in the operating room and slow the analysis workflow in current clinical procedures. There is a great need in the operating room for a system that could efficiently provide a ready-to-use device to an operator within a few seconds.

Exemplary embodiments therefore provide two different ways to eliminate contamination between each procedure by either automatically changing to a completely new device and conduit and/or including a quick washing cycle to clean or refresh the previously used device and conduit. These two approaches are not independent and can be used separately or in combination. For example, an exchange step may be carried out while a previously used device and conduit may be undergoing a cleaning step.

Certain embodiments include an apparatus comprising: a cassette comprising a plurality of sample acquisition probes; and a sample processing instrument configured to receive a sample, where: the cassette is coupled to the sample processing instrument; a first sample acquisition probe is in fluid communication with the sample processing instrument when the cassette is in a first orientation; a second sample acquisition probe is in fluid communication with the sample processing instrument when the cassette is in a second orientation; and the cassette can be moved from the first orientation to the second orientation while the cassette is coupled to the sample processing instrument.

In particular embodiments, the sample processing instrument is a mass spectrometer. In some embodiments, the cassette rotates from the first orientation to the second orientation. In specific embodiments, the cassette moves linearly from the first orientation to the second orientation. Certain embodiments further comprise a first plurality of conduits, where: each sample acquisition probe is in fluid communication with an individual conduit of the first plurality of conduits; and each individual conduit of the first plurality of conduits is configured to place a single sample acquisition probe in fluid communication with the sample processing instrument when the cassette is oriented to align the individual conduit with the sample processing instrument. In particular embodiments, each conduit between each sample acquisition probe and the sample processing instrument comprises a valve configured to restrict flow through the conduit. Some embodiments, further comprise: a first chamber comprising a solvent; and a gas supply. In specific embodiments, the gas supply provides air, nitrogen or carbon dioxide to the probe (e.g., from a gas canister or the ambient air). In certain embodiments, the gas supply is a pressurized gas supply. In a further embodiment, the gas supply is the ambient air and the apparatus comprises a valve or conduit that is open to the ambient air. In particular embodiments, the pressurized gas supply provides a gas to the probe at a pressure between 0.1 psig and 5.0 psig, or more particularly between 0.5 psig and 2.5 psig. In some embodiments, the pressurized gas supply provides a gas to the probe at a pressure less than 100 psig.

In specific embodiments, the solvent comprises water, sterile water, ethanol, and/or an aqueous mixture including from 1 to 25% ethanol. Some embodiments further comprise: a second plurality of conduits in fluid communication with the first chamber and the plurality of sample acquisition probes; and a third plurality of conduits in fluid communication with the gas supply (e.g., a gas canister or the ambient air) and the plurality of sample acquisition probes. In certain embodiments, each sample acquisition probe in the plurality of sample acquisition probes comprises a reservoir, a first conduit, a second conduit and a third conduit, where: the first conduit is in fluid communication with the first chamber; the second conduit is in fluid communication with the gas supply; and the third conduit is in fluid communication with the sample processing instrument. In specific embodiments each sample acquisition probe in the plurality of sample acquisition probes comprises a funnel-shaped chamber in fluid communication with the reservoir, the first conduit, the second conduit and the third conduit. In certain embodiments, the funnel-shaped chamber comprises a larger end and a smaller end; and the larger end of the funnel-shaped chamber is proximal to the reservoir. Particular embodiments further comprise: a second chamber comprising a cleaning fluid; and a conduit in fluid communication with the second chamber and the plurality of sample acquisition probes. In some embodiments, the sample acquisition probe is, or is comprised in, the cannula of a surgical instrument. In specific embodiments, the surgical instrument is a laparoscope, a trocar needle, a biopsy guide, or a multiple-lumen catheter. In certain embodiments, the surgical instrument manually operated. In particular embodiments, the surgical instrument is robotic. In some embodiments, the surgical instrument comprises a tracking probe that can be detected by imaging. In specific embodiments, the imaging comprises visual, fluorescent, US, CT, MRI or OCT imaging.

In certain embodiments, each sample acquisition probe of the plurality of sample acquisition probes comprises a distal probe end and the distal probe end comprises a shutter that can be closed to prevent fluid communication outside of the sample acquisition probe. In particular embodiments, the shutter is a balloon that can be inflated to prevent fluid communication outside of the probe. In some embodiments, the balloon can be inflated with a gas or a liquid. In specific embodiments, the shutter is door that can be closed to prevent fluid communication outside of the probe. In certain embodiments, the shutter is configured such that is can be opened and closed multiple times. In particular embodiments, the shutter is controlled manually. In some embodiments, the shutter is controlled robotically. In certain embodiments, the sample processing instrument is in electronic communication with a computer that can provide sample analysis. In particular embodiments, the computer provides a visual or auditory read-out of the sample analysis. In specific embodiments, each sample acquisition probe of the plurality of sample acquisition probes comprises a tracking device or dye to track a location of the probe.

Certain embodiments include an apparatus comprising: a cassette comprising a plurality of medical devices; and a processing instrument coupled to the cassette, where: the medical devices are configured to contact tissue; the processing instrument is configured to receive tissue from the cassette; a first medical device of the plurality of medical devices is in fluid communication with the processing instrument when the cassette is in a first orientation; a second medical device is in fluid communication with the processing instrument when the cassette is in a second orientation; and the cassette can be moved from the first orientation to the second orientation while the cassette is coupled to the processing instrument. In particular embodiments, the plurality of medical devices comprises a plurality of sample acquisition probes. In some embodiments, the processing instrument is a mass spectrometer. In specific embodiments, the cassette rotates from the first orientation to the second orientation. In certain embodiments, the cassette moves linearly from the first orientation to the second orientation. Particular embodiments, further comprise a first plurality of conduits, where: each medical device is in fluid communication with an individual conduit of the first plurality of conduits; and each individual conduit of the first plurality of conduits is configured to place a single medical device in fluid communication with the processing instrument when the cassette is oriented to align the individual conduit with the processing instrument.

In certain embodiments, each conduit between each medical device and the processing instrument comprises a valve configured to restrict flow through the conduit. Some embodiments further comprise: a first chamber comprising a solvent; and a gas supply. Specific embodiments further comprise: a second plurality of conduits in fluid communication with the first chamber and the plurality of medical devices; and a third plurality of conduits in fluid communication with the gas supply and the plurality of medical devices. Certain embodiments further comprise: a second chamber comprising a cleaning fluid; and a conduit in fluid communication with the second chamber and the plurality of medical devices.

Particular embodiments include a method for exchanging medical instruments during a medical procedure, where the method comprises: acquiring a first sample acquisition probe from a cassette comprising a plurality of sample acquisition probes, wherein the first sample acquisition probe is acquired from the cassette when the cassette is in a first orientation; obtaining a first tissue sample with the first sample acquisition probe; changing the orientation of the cassette comprising the plurality of sample acquisition probes from a first orientation to a second orientation; acquiring a second sample acquisition probe from the cassette comprising a plurality of sample acquisition probes, where the second sample acquisition probe is acquired from the cassette when the cassette is in a second orientation; and obtaining a second tissue sample with the second sample acquisition probe.

Some embodiments further comprise priming the sample acquisition probe with solvent prior to obtaining the first tissue sample. In specific embodiments, changing the orientation of the cassette comprising the plurality of sample acquisition probes from a first orientation to a second orientation comprises rotating the cassette. In certain embodiments, changing the orientation of the cassette comprising the plurality of sample acquisition probes from a first orientation to a second orientation comprises linearly translating the cassette. In particular embodiments, obtaining the first tissue sample with the first sample acquisition probe comprises: applying a first fixed volume of a solvent to a first tissue site through the cannula of a surgical instrument; and collecting the applied solvent to obtain a first liquid sample.

In some embodiments, obtaining the second tissue sample with the second sample acquisition probe comprises: applying a second volume of the solvent to a second tissue site through the cannula of the surgical instrument; and collecting the applied solvent to obtain a second liquid sample. In specific embodiments, the first volume of solvent and the second volume of solvent are not applied as a spray. In certain embodiments, the first volume of solvent is applied as a first droplet and wherein the second volume of solvent is applied as a second droplet. In particular embodiments, the surgical instrument is a laparoscope, a trocar needle, or a biopsy guide. In some embodiments, the surgical instrument is manually operated. In specific embodiments, the surgical instrument is robotic. Certain embodiments further comprise applying a dye to the first tissue site and to the second tissue site. Particular embodiments, further comprise imaging the first tissue site and the second tissue site. In some embodiments, the imaging comprises visual, fluorescent, US, CT, MRI or OCT imaging. In specific embodiments, the first volume of solvent and the second volume of solvent are applied using a pressure of less than 100 psig. In certain embodiments, the fixed or discrete volume of a solvent is applied at using a pressure of less than 10 psig. In particular embodiments, the fixed or discrete volume of a solvent is applied at using a mechanical pump to move the solvent through a solvent conduit. In some embodiments, collecting the applied solvent comprises applying a negative pressure to pull the sample into a collection conduit and/or applying a gas pressure to push the sample into a collection conduit.

In specific embodiments, the solvent is applied through a solvent conduit that is separate from the collection conduit. In certain embodiments, the gas pressure is applied through a gas conduit that is separate from the solvent conduit and the collection conduit. In particular embodiments, applying a gas pressure to push the sample into the collection conduit comprises applying a pressure of less than 100 psig. In some embodiments, the method produces no detectable physical damage to the tissue. In specific embodiments, the method does not involve application of ultrasonic or vibrational energy to the tissue. In certain embodiments, the solvent is sterile. In some embodiments, the solvent is pharmaceutically acceptable formulation. In specific embodiments, the solvent is an aqueous solution. In certain embodiments, the solvent is sterile water. In particular embodiments, the solvent consists essentially of water. In some embodiments, the solvent comprises from about 1 to 20% of an alcohol. In specific embodiments, the alcohol comprises ethanol.

In certain embodiments, the first volume of solvent is between about 0.1 and 100 µL and wherein the second volume of solvent is between about 0.1 and 100 µL. In particular embodiments, the first volume of solvent is between about 1 and 50 µL and the second volume of solvent is between about 1 and 50 µL. In some embodiments, collecting the applied solvent is between 0.1 and 30 seconds after the applying step. In specific embodiments, collecting the applied solvent is between 1 and 10 seconds after the applying step. In certain embodiments, the first tissue site is an internal tissue site that is being surgically assessed and wherein the second tissue site is an internal tissue site that is being surgically assessed. In particular embodiments, the first liquid sample and the second liquid sample are collected with a probe. Some embodiments, further comprise collecting a plurality of liquid samples from a plurality of tissue sites. In specific embodiments, the plurality of tissue sites comprises 2, 3, 4, 5, 6, 7, 8, 9 or 10 tissues sites. In certain embodiments, the plurality of tissue sites surrounds a section of tissue that has been surgically resected. In particular embodiments, the resected tissue is a tumor. In some embodiments, the method is an intraoperative or postoperative method. Specific embodiments further comprise subjecting the first tissue sample and the second tissue sample to mass spectrometry analysis. In certain embodiments, the mass spectrometry comprises ambient ionization MS.

In particular embodiments, the first tissue sample and the second tissue sample to mass spectrometry analysis comprises determining a first profile corresponding to the first tissue site and a second profile corresponding to the second tissue site. Some embodiments, further comprise comparing the first profile and the second to a reference profile to identify tissue sites that include diseased tissue. Specific embodiments further comprise resecting tissue sites that are identified to include diseased tissue. In certain embodiments, resecting tissue sites comprises laser ablation. Specific embodiments, further comprise comparing the first profile and the second to a reference profile to determine the tissue type at the first tissue site and the second tissue type. Certain embodiments further comprise resecting tissues of an identified type. In particular embodiments, the identified tissue type is a cancerous tissue or a non-cancerous type of organ tissue. In specific embodiments, the method is performed using an apparatus in accordance with exemplary embodiments disclosed herein.

Certain embodiments include an apparatus for producing samples for mass spectrometry analysis, where the apparatus comprises: a chamber comprising a solvent; a gas supply; a mass spectrometer; and a probe comprising a reservoir, a first conduit, a second conduit, a third conduit, and a vacuum port, where: the first conduit is in fluid communication with the chamber; the second conduit is in fluid communication with gas supply; and the third conduit is in fluid communication with the mass spectrometer. In particular embodiments, the vacuum port is configured as an indented ring that extends around a perimeter of the probe. In some embodiments, the vacuum port is configured as an end of a channel that extends to a surface of the probe configured to contact tissue. In specific embodiments, the vacuum port is one of a plurality of vacuum ports. In certain embodiments, the plurality of vacuum ports are in fluid communication with a pneumatic channel multiplexer. In some embodiments, the plurality of vacuum ports are in fluid communication with the pneumatic channel multiplexer via a plurality of pneumatic channels. In specific embodiments, the pneumatic channel multiplexer is a circumferential ring extending around the device. Certain embodiments further comprise a vacuum source in fluid communication with the vacuum port. In particular embodiments, the gas supply is a pressurized gas supply.

Specific embodiments include an apparatus comprising: a plurality of sample acquisition probes coupled to a plurality of conduits, where the plurality of conduits comprises solvent supply conduits and sample acquisition conduits; one or more chambers containing solvent; a plurality of valves configured to control flow of the solvent through the solvent supply conduits; and a sample processing instrument configured to receive a sample, where: each of the plurality of sample acquisition probes and solvent supply conduits can be individually coupled to the one or more chambers containing solvent; and each of the plurality of sample acquisition probes and sample acquisition conduits can be individually coupled to the sample processing instrument. In certain embodiments, the sample processing instrument is a mass spectrometer with an inlet port; the apparatus comprises a pump in fluid communication with the one or more chambers containing solvent; each solvent supply conduit is configured to be coupled to the pump via a Luer lock mechanism; and/or each sample acquisition conduit is configured to be directly coupled to the inlet of the mass spectrometer via a Luer lock mechanism.

In particular embodiments, each of the plurality of sample acquisition conduits can be individually coupled to the sample processing instrument via a quick release mechanism. In some embodiments, the quick release mechanism is a Luer lock or a friction fit coupling. In specific embodiments, each of the plurality of solvent supply conduits can be individually coupled to the solvent supply by a quick release mechanism. In certain embodiments, the quick release mechanism is a Luer lock or a friction fit coupling. In particular embodiments, each of the plurality of sample acquisition probes and sample acquisition conduits can be individually coupled to the sample processing instrument via a quick release mechanism. In some embodiments, each of the plurality of sample acquisition probes and sample acquisition conduits can be individually coupled to the sample processing instrument via a friction fit coupling. In specific embodiments, each of the plurality of sample acquisition probes and sample acquisition conduits can be individually coupled to the sample processing instrument via a Luer Lock fitting.

Certain embodiments include a method of obtaining a plurality of samples, the method comprising: obtaining an apparatus as disclosed herein; coupling a first solvent supply conduit to a first sample acquisition probe and to the one or more chambers containing solvent; coupling a first sample acquisition conduit in fluid communication with the first sample acquisition probe to the sample processing instrument; obtaining a first sample with the first sample acquisition probe; de-coupling the first sample acquisition from the sample processing instrument; analyzing the first sample with the sample processing equipment; coupling a second solvent supply conduit in fluid communication with a second sample acquisition probe to the one or more chambers containing solvent; coupling a second sample acquisition conduit in fluid communication with the second sample acquisition probe to the sample processing instrument; obtaining a second sample with the second sample acquisition probe; and analyzing the second sample with the sample processing equipment.

Particular embodiments further comprise priming the first sample acquisition probe with solvent prior to obtaining the first tissue sample. In certain embodiments, coupling the second sample acquisition conduit to the sample processing instrument is performed while the sample processing instrument is analyzing the first sample. Particular embodiments further comprise: de-coupling the second sample acquisition from the sample processing instrument; coupling a third solvent supply conduit in fluid communication with a third sample acquisition probe to the one or more chambers containing solvent; coupling a third sample acquisition conduit in fluid communication with the third sample acquisition probe to the sample processing instrument; obtaining a third sample with the third sample acquisition probe; and analyzing the third sample with the sample processing equipment. Some embodiments further comprise: de-coupling the second sample acquisition from the sample processing instrument; coupling the first solvent supply conduit in fluid communication with the first sample acquisition probe to the one or more chambers containing solvent; coupling the first sample acquisition conduit in fluid communication with the first sample acquisition probe to the sample processing instrument; obtaining a third sample with the first sample acquisition probe; and analyzing the third sample with the sample processing equipment.

Specific embodiments further comprise: de-coupling the second sample acquisition from the sample processing instrument; coupling a third solvent supply conduit in fluid communication with the first sample acquisition probe to the one or more chambers containing solvent; coupling a third sample acquisition conduit in fluid communication with the first sample acquisition probe to the sample processing instrument; obtaining a third sample with the first sample acquisition probe; and analyzing the third sample with the sample processing equipment.

Certain embodiments include a method for cleaning a medical instrument during a medical procedure, where the method comprises: obtaining a first tissue sample with a first sample acquisition probe when the first sample acquisition probe is in a first location; moving the first sample acquisition probe to a second location; cleaning the first sample acquisition probe when the first sample acquisition probe is in the second location; moving the first sample acquisition probe to the first location; and obtaining a second tissue sample with the first sample acquisition probe when the first sample acquisition probe is in the first location. In particular embodiments, the first sample acquisition probe is located in a cassette, and moving the first sample acquisition probe to the second location comprises rotating the cassette.

In some embodiments, washing the first sample acquisition probe comprises directing a cleaning fluid from a chamber to the first sample acquisition probe via a conduit. In specific embodiments, obtaining the first tissue sample with the first sample acquisition probe comprises: applying a first fixed volume of a solvent to a first tissue site through the cannula of a surgical instrument; and collecting the applied solvent to obtain the first tissue sample. In particular embodiments, obtaining the second tissue sample with the first sample acquisition probe comprises: applying a second fixed volume of the solvent to a second tissue site through the cannula of the surgical instrument; and collecting the applied solvent to obtain the first tissue sample.

In a first embodiment there is provided an apparatus and method for obtaining a mass spectrometry profile comprising using a probe to apply a fixed or discrete volume of a solvent to an assay site (e.g., a tissue site); using the probe to collect the applied solvent to obtain a liquid sample; and subjecting the liquid sample to mass spectrometry analysis. In further embodiment a method is provided for assessing tissue samples comprising obtaining a plurality of liquid samples from a plurality of tissue sites in a subject and subjecting the plurality of liquid samples to mass spectrometry.

Still a further embodiment provides an apparatus for obtaining or producing samples (e.g., from tissues) for mass spectrometry analysis, the apparatus comprising: a chamber comprising a solvent; a gas supply; a mass spectrometer; a probe comprising a reservoir, a first conduit, a second conduit and a third conduit, wherein: the reservoir is in fluid communication with the first conduit, the second conduit and the third conduit; the first (solvent) conduit is in fluid communication with the chamber; the second (gas) conduit is in fluid communication with gas supply (e.g., a gas canisters or the ambient air); and the third (collection) conduit is in fluid communication with the mass spectrometer. In some aspects, the gas supply can be a pressurized gas supply. In further aspects, the gas supply can comprise the atmosphere surrounding the apparatus. In some aspects, the probe is, or is comprised in, the cannula of a surgical instrument. In further aspects, the surgical instrument may be a laparoscope, trocar needle, biopsy guide, or multiple-lumen catheter. In certain aspects, the surgical instrument manually operated. In other aspects, the surgical instrument is robotic.

In yet still further aspects, the probe comprises a distal probe end and the distal probe end comprises a shutter that can be closed to prevent fluid communication outside of the probe. In some aspects, the shutter is a balloon that can be inflated to prevent fluid communication outside of the probe. In certain aspects, the balloon can be inflated with a gas or a liquid. In specific aspects, the shutter is a door that can be closed to prevent fluid communication outside of the probe. In other aspects, the shutter is configured such that is can be opened and closed multiple times. The shutter may be controlled manually or robotically. In several aspects, the first, second or third conduit is more than 1 meter in length. In additional aspects, the first conduit is in fluid communication with the third conduit; and the second conduit is in fluid communication with the third conduit. In further specific aspects, the first conduit is disposed within the third conduit. In other aspects, the second conduit is disposed within the third conduit.

In certain specific aspects, the first conduit and the second conduit are disposed within the third conduit. In further aspects, the first conduit comprises a first distal end; the second conduit comprises a second distal end; the third conduit comprises a third distal end; and the first distal end and the second distal end are located within the third conduit. In some aspects, the third distal end is located within the probe. In another aspect, the first distal end is located a first distance from the distal probe end; the second distal end is located a second distance from the distal probe end; the third distal end is located a third distance from the distal probe end; the first distance is greater than the third distance; and the second distance is greater than the third distance. In an additional aspect, the first distal end and the second distal end terminate proximal to a sample collection region of the third conduit. In certain aspects, the sample collection region is located between the first and second distal ends and the third distal end. In further specific aspects, the sample collection region is in fluid communication with the mass spectrometer via the third conduit. In some additional aspects, the apparatus further comprises a control system configured to control; a solvent flow from the chamber through the first conduit to the first distal end; a gas flow from the gas supply through the second conduit to the second distal end; and a sample flow through the third conduit to the mass spectrometer.

In yet still further aspects, the apparatus may additionally comprise a fourth conduit, wherein the first conduit, the second conduit and the third conduit are each in fluid communication with the fourth conduit. In some aspects, the apparatus may further comprise a first valve configured to control flow between the first conduit and the fourth conduit; and a second valve configured to control flow between the second conduit and the fourth conduit. In an additional aspect, the apparatus may further comprise a third first valve configured to control flow between the third conduit and the fourth conduit. In still additional aspects, the gas supply provides air, nitrogen or carbon dioxide to the probe. In certain aspects, the gas supply is a pressurized gas supply that provides a gas to the probe at a pressure between 0.1 psig and 5.0 psig. In other aspects, the pressurized gas supply provides a gas to the probe at a pressure between 0.5 psig and 2.5 psig. In specific aspects, the pressurized gas supply provides a gas to the probe at a pressure less than 100 psig. In some aspects, the gas for use in an apparatus of the embodiments may be provided by a pressurized gas supply. In further aspects, the gas can be pumped into an apparatus. Likewise, in some aspects, the gas can be pulled through an apparatus by use of a vacuum. In some aspects, the vacuum is provided by the mass spectrometer inlet. In further aspects, an additional vacuum system is employed.

In some aspects, the solvent comprises water. In more specific aspects, the solvent comprises sterile water. In several aspects, the solvent comprises ethanol. In certain specific aspects, the solvent comprises an aqueous mixture including from 1 to 25% ethanol.

In still further aspects, the probe comprises a tracking device or dye to track a location of the probe. In additional aspects, the apparatus may further comprise a control system configured to control: a solvent flow from the chamber through the first conduit; a gas flow from the gas supply through the second conduit; and a sample flow through the third conduit to the mass spectrometer. In some aspects, the control system is configured to: control the solvent flow at a flow rate between 200 and 5000 microliters per minute for a period of time between 1 and 3 seconds; control the gas flow at a flow rate between 0.1 and 15 psig for a period of time between 5 and 50 seconds; and/or control the sample flow for a period of time between 5 and 50 seconds. In certain aspects, the control system comprises programing that initiates solvent flow.

In additional aspects, the mass spectrometer is in electronic communication with a computer that can provide sample analysis. In some aspects, the computer provides a visual or auditory read-out of the sample analysis. In further aspects, the apparatus may additionally comprise a waste container in fluid communication with the third conduit. In certain aspects, the apparatus may further comprise a valve configured to diverge a fluid from the third conduit to the waste container. In other aspects, the apparatus may further comprise a pump configured to remove contents of the waste container. In still further aspects, the apparatus may comprise a pump in fluid communication with the third conduit. In some aspects, the pump is configured to increase the velocity of the contents within the third conduit. In several aspects, the apparatus may further comprise a heating element coupled to the third conduit. In a specific aspect, the heating element is a heating wire.

In yet still further aspects, the apparatus may comprise an ionization device in fluid communication with the third conduit. In certain aspects, the ionization device is an electrospray ionization (ESI) device. In other aspects, the ionization device is an atmospheric pressure chemical ionization (APCI) device. In some aspects, the ionization device is to form a spray proximal to an inlet for mass spectrometer. In several aspects, the third conduit is not directly coupled to the mass spectrometer. In specific aspects, the apparatus may further comprise a venturi device in fluid communication with the third conduit. In certain aspects, the apparatus does not include device for application of ultrasonic or vibrational energy.

In a further embodiment there is provided a method for assessing tissue samples from a subject comprising (a) applying a fixed or discrete volume of a solvent to a tissue site in the subject through the cannula of a surgical instrument; (b) collecting the applied solvent to obtain a liquid sample; and (c) subjecting the sample to mass spectrometry analysis. In some aspects, the fixed or discrete volume of a solvent is not applied as a spray. In other aspects, the fixed or discrete volume of a solvent is applied as a droplet. In certain aspects, the surgical instrument is a laparoscope, trocar needle, or biopsy guide. The surgical instrument may be manually operated or robotic.

In further aspects, the cannulas comprised in a probe having a distal probe end and the distal probe end comprises a shutter that can be closed to prevent fluid from passing out of the cannula of the probe. In some aspects, the shutter is a balloon that can be inflated to prevent fluid communication outside of the probe. In specific aspects, the balloon can be inflated with a gas. In certain aspects, the shutter is a door than can be closed to prevent fluid communication outside of the probe. For example, the shutter can be an iris diaphragm, a mechanical closure, gate, or tapenade. In some aspects, the shutter can be manually controlled or may be automated. For example, in some aspects, the shutter may be on a timer that activates the shutter after solvent has been in contact with the tissue site for a predetermined time period (e.g., at least about 1, 2, or 3 seconds). In still further aspects, the fixed or discrete volume of a solvent is applied at using a pressure of less than 100 psig. In other aspects, the fixed or discrete volume of a solvent is applied at using a pressure of less than 10 psig. In some aspects, the fixed or discrete volume of a solvent is applied using a mechanical pump to move the solvent through a solvent conduit. In certain aspects, collecting the applied solvent comprises applying a negative pressure to pull the sample into a collection conduit and/or applying a gas pressure to push the sample into a collection conduit. In other aspects, collecting the applied solvent comprises applying a negative pressure to pull the sample into a collection conduit and applying a positive pressure to push the sample into a collection conduit. In certain specific aspects, the solvent is applied through a solvent conduit that is separate from the collection conduit. In further aspects, the gas pressure is applied through a gas conduit that is separate from the solvent conduit and the collection conduit. In still other aspects, applying a gas pressure to push the sample into a collection conduit comprises applying a pressure of less than 100 psig.

In yet still further aspects, the method produces no detectable physical damage to the tissue. In some aspects, the method does not involve application of ultrasonic or vibrational energy to the tissue. In certain aspects, the solvent may be sterile. In specific aspects, the solvent may be a pharmaceutically acceptable formulation, and further an aqueous solution, and still further sterile water. In further specific aspects, the solvent consists essentially of water. In other aspects, the solvent comprises from about 1 to 20% of an alcohol. In some aspects, the alcohol comprises ethanol. In still additional aspects, the discrete volume of solvent is between about 0.1 and 100 µL. In certain aspects, the discrete volume of solvent is between about 1 and 50 µL. In further aspects, collecting the applied solvent is between 0.1 and 30 seconds after the applying step. In another aspect, collecting the applied solvent is between 1 and 10 seconds after the applying step. In some aspects, the tissue site in an internal tissue site that is being surgically assessed.

In still further aspects, the method additionally comprises collecting a plurality liquid samples from a plurality of tissue sites. In certain aspects, the liquid samples are collected with a probe. In specific aspects, the probe is washed between collection of the different samples. In some aspects, the probe is disposable and is changed between collection of the different samples. In another aspect, the probe comprises a collection tip and further comprising ejecting the collection tip from the probe after the liquid samples are collected. In further aspects, the plurality of tissue sites comprises 2, 3, 4, 5, 6, 7, 8, 9 or 10 tissues sites. In an additional aspect, the plurality of tissue sites surrounds a section of tissue that has been surgically resected. In some aspects, the resected tissue is a tumor. In other aspects, the method is further defined as an intraoperative or post-operative method. In certain aspects, the mass spectrometry comprises ambient ionization MS. In certain specific aspects, subjecting the sample to mass spectrometry analysis comprises determining a profile corresponding to the tissue site. In a further aspect, the method comprises comparing the profile to a reference profile to identify tissue sites that include diseased tissue. Still a further aspect comprises resecting tissue sites that are identified to include diseased tissue. In another aspect, the method is performed using an apparatus in accordance with the embodiments and aspects described above.

In further aspects, the mass spectrometer is in communication with a computer that provides a sample analysis. In certain aspects, the results of each sample analysis are provided by a visual or auditory output from the computer. For example, the results of each sample analysis by the computer can be indicated by a differently colored light that is illuminated or by a different frequency of sound produced.

In some aspects, the mass spectrometer is a mobile the mass spectrometer. In further aspects, the mass spectrometer can comprise an uninterruptable power supply (e.g., a battery power supply). In still further aspects, the mass spectrometer comprises an inlet that may be closed to keep instrument vacuum. In yet further aspects, the mass spectrometer is separated from the probe by a mesh filter (e.g., to block contamination).

In some aspects, the reservoir is configured to form a droplet of the solvent. In certain aspects, the pressurized gas supply provides a gas to the probe at a pressure between 0.1 psig and 5.0 psig. In further aspects, the pressurized gas supply provides a gas to the probe at a pressure between 0.5 psig and 2.5 psig. In several aspects, the pressurized gas supply provides air to the probe. In other aspects, the pressurized gas supply provides an inert gas such as nitrogen or carbon dioxide to the probe. In some aspects, a gas supply for use according to the embodiments is at atmospheric pressure. For example, the conduit for delivery of gas may be supplied by the atmosphere around the apparatus.

In additional aspects, the apparatus further comprises a pump configured to transfer the solvent from the chamber to the first conduit. In further aspects, the apparatus may comprise a first valve configured to control a flow from the third conduit to the mass spectrometer. In some aspects, the third conduit is under a vacuum when the first valve is in the open position. In other aspects, the apparatus may comprise a second valve configured to control a flow of gas (e.g., pressurized gas) through the second conduit.

In certain aspects, the solvent may comprise water and/or ethanol. In several aspects, the probe is formed from polydimethylsiloxane (PDMS) and/or polytetrafluoroethylene (PTFE). In some aspects, the probe is disposable. In particular aspects, the probe may include a collection tip that is ejectable (e.g. capable of being ejected from the probe). In further aspects, the probe comprises a tracking device configured to track a location of the probe. In some aspects, the reservoir has a volume between 1 microliter and 500 microliters, between about 1 microliter and 100 microliters or between about 2 microliters and 50 microliters. In additional aspects, the reservoir has a volume between 5.0 microliters and 20 microliters.

In still further aspects, the apparatus may additionally comprise a control system configured to control: a solvent flow (e.g., flow of a fixed or discrete volume of solvent) from the chamber through the first conduit to the reservoir; a gas flow from the gas supply through the second conduit to the reservoir; and a sample flow from the reservoir through the third conduit to the mass spectrometer. In some aspects, the control system is configured to: control the solvent flow at a flow rate between 100 and 5000 microliters per minute (e.g., between 200 and 400 microliters per minute) for a period of time between 1 and 3 seconds; control the gas flow at a flow rate between 1 and 10 psig for a period of time between 10 and 15 seconds; and control the sample flow for a period of time between 10 and 15 seconds. For example, in some aspects, the control system comprises a trigger or button to initiate solvent flow. In further aspects, the control system comprises a pedal (i.e., that can be operated by foot action) to initiate solvent flow. A skilled artisan will recognize that the lengths of the first and/or second conduit may be adjusted to fit the particular use of the system. In yet further aspects, the control system is configured to control: a solvent flow (e.g., flow rate for a fixed period of time) from the chamber through the first conduit to the reservoir. In further aspects, an apparatus of the embodiments does not include a device for producing ultrasonic or vibrational energy (e.g., in sufficient amounts to disrupt tissues).

A further embodiment provided a method for assessing tissue samples from a subject comprising applying a solvent to a tissue site on the subject, collecting the applied solvent to obtain a liquid sample, and subjecting the sample to mass spectrometry analysis. In certain aspects, the solvent may be sterile. In some aspects, the solvent is pharmaceutically acceptable formulation. In specific aspects, the solvent is an aqueous solution. For example, the solvent may be sterile water or consist essentially of water. In other aspects, the solvent may comprise from about 1% to 5%, 10%, 15%, 20%, 25% or 30% of an alcohol. In some aspects, the solvent comprises 0.1% to 20% of an alcohol, 1% to 10% of an alcohol or 1% to 5% 1% to 10% of an alcohol (e.g., ethanol). In some cases, the alcohol may be ethanol.

In some aspects, applying the solvent to the tissue comprises applying a discrete volume of solvent to the tissue site. In some aspect, the solvent is applied in a single droplet. In a further aspect, the solvent is applied in a discrete number of droplets from 1 to 10. In some embodiments, the solvent is applied to the sample from the reservoir via a channel independent of the gas. In further embodiments, the solvent is applied to the sample under low pressure. For example, in some aspects, the solvent is applied by a mechanical pump such that solvent is applied to the tissue site (e.g., moved into a reservoir where it is in contact with the tissue site) with minimal force thereby exerting minimal pressure (and producing minimal damage) at a tissue site. The low pressure may be less than 100 psig, less than 90 psig, less than 80 psig, less than 70 psig, less than 60 psig, less than 50 psig, or less than 25 psig. In some embodiments, the low pressure is from about 0.1 psig to about 100 psig, from about 0.5 psig to about 50 psig, from about 0.5 psig to about 25 psig, or from about 0.1 psig to about 10 psig. In particular aspects, the discrete volume of solvent is between about 0.1 and 100 µL, or between about 1 and 50 µL. In further aspects, collecting the applied solvent is between 0.1 and 30 seconds after the applying step. In a specific aspect, collecting the applied solvent is between 1 and 10 seconds after the applying step (e.g., at least 1, 2, 4, 5, 6, 7, 8 or 9 seconds). In further aspects, a method of the embodiments does not involve application of ultrasonic or vibrational energy to a sample or tissue. In some aspects, the tissue site in an internal tissue site that is being surgically assessed.

In a further aspect, a method of the embodiments comprises applying a fixed or discrete volume of a solvent (e.g., using mechanical pump) to a tissue site through a solvent conduit. In some aspects, the fixed or discrete volume of a solvent is moved through a solvent conduit into a reservoir where it is in direct contact with a tissue site (e.g., for 0.5-5.0 seconds). In further aspects, collecting the applied solvent comprises applying a negative pressure to pull the sample into a collection conduit and/or applying a gas pressure to push the sample into a collection conduit. In some aspects, the solvent is applied through a solvent conduit that is separate from the collection conduit. In further aspects, wherein a gas pressure is applied to push the sample into the collection conduit the gas pressure is applied through a gas conduit that is separate from the solvent conduit and the collection conduit. In certain aspects, wherein a gas pressure is applied to push the sample into the collection conduit, the applied gas pressure of less than 100 psig. For example, the gas pressure is preferably less than 10 psig, such as 0.1 to 5 psig. In still further aspects, a method of the embodiments is defined as producing no detectable physical damage to the tissue being assessed.

In still further aspects, the method may additionally comprise collecting a plurality liquid samples from a plurality of tissue sites. In some cases, the device (e.g., the probe) used to collect the samples is washed between each sample collection. In other aspects, a device used to collect the samples includes a disposable collection tip (probe) that can be changed between each sample collection. In particular aspects, the collection tip may be ejectable (e.g. capable of being ejected from the device). In certain aspects, the plurality of tissue sites comprise 2, 3, 4, 5, 6, 7, 8, 9, 10 or more tissues sites in vivo. In another aspect, the plurality of tissue sites surround a section of tissue that has been surgically resected (e.g., ex vivo). In a specific aspect, the resected tissue is a tumor. In some aspects, the method may be defined as an intraoperative method.

A further embodiment provides a method of identifying a sampled tissue site and a method to communicate location of the site to the device (probe) operator. Identification of a sampled tissue site allows the operator to access the molecular information recorded at sampled tissue site at a time after sampling molecules collected from the tissue. At least three types of identification approaches are recognized. In the first approach, an exogenous material is attached to the sampled tissue site that identifies the sampled molecular information. In a second approach, the device (probe) is equipped with a tracking sensor/emitter that allows recording the location of the probe (device) and communication to an imaging device when the molecular information is sampled. In a third approach, the tissue region is modified so that the site may be easily identified after harvesting tissue molecules. In the first approach, materials that may be attached to the sampled tissue site include, for example, a suture, a surgical clip, a biocompatible polymer that adheres to the tissue, or an RFID chip that is attached to a magnetic bead that allows easy reading and removal. In the second approach type, the probe may contain an RF emitter that is part of a RF surgical tracking system, an ultrasound emitter or reflector that is part of an intra-operative US imaging system. In this second approach, when the operator initiates collection of tissue molecules, the tracking system records location of the probe in the associated imaging system (e.g., RF, US, CT, MRI) that may be in communication with the device. The operator may then identify any of the sampled tissue sites at a later time by referring to the recorded image(s) that can indicate the location of sampled sites to the operator. In the third approach, the tissue is modified. In this third approach, a laser source in communication with the probe may be used to ablate or coagulate a pattern into the tissue that identifies the sampled site. Any of these three approaches may be combined. For example, approach 1, 2 and 3 could be combined wherein an exogenous material is attached to the tissue site after harvesting tissue molecules and a laser patterns the exogenous tissue while an RF sensor records location of the harvest location and communicates to the imaging device.

In yet still further aspects, the mass spectrometry comprises ambient ionization MS. As disclosed herein a probe in contact with a tissue site can be in fluid communication with the MS via a conduit. In some aspects, conduit between the probe and tissue site is less than about 10 m, 8 m, 6 m or 4 m from MS. In further aspects, the conduit is between about 0.5, 1.0, 1.5, 2.0, 2.5, 3.0 and 4.0 m in length. In several aspects, subjecting the sample to mass spectrometry analysis may comprise determining a profile corresponding to the tissue site. In another aspect, the method may additionally comprise comparing the profile to a reference profile to identify tissue sites that include diseased tissue. In other aspects, the method also comprises resecting tissue sites that are identified to include diseased tissue. In some aspects, the method is performed using an apparatus in accordance with any of the embodiments and aspects described above.

In a further embodiment, the invention provides an ex vivo method for assessing tissue samples comprising obtaining a plurality of liquid samples from a plurality of tissue sites in a subject, subjecting the plurality of liquid samples to mass spectrometry to obtain a plurality of profiles corresponding to the tissue sites, and comparing the plurality of profiles to reference profiles to identify tissue sites that include diseased tissue. In certain aspects, the liquid samples are comprised in a solvent. In further aspects, the diseased tissues comprise cancer cells.

In some aspects of the embodiments, the diseased tissue sites for assessment by methods and devices of the embodiments comprise (or are suspected of comprising) cancer cells. Cancer cells that may be assessed according to the embodiments include but are not limited to cells or tumor tissues from a thyroid, parathyroid, lymph node, bladder, blood, bone, bone marrow, brain, breast, colon, esophagus, gastrointestine, gum, head, kidney, liver, lung, nasopharynx, neck, ovary, pancreas, prostate, skin, stomach, testis, tongue, or uterus (or tissues surrounding such tumors). In some aspects, the cancer may be a neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant;

synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; or paragranuloma. In further aspects the cancer is a thyroid cancer, brain cancer (e.g., a glioma), a prostate cancer, a breast cancer (e.g., a triple negative breast cancer), a pancreatic cancer (e.g., a pancreatic ductal adenocarcinoma), acute myeloid leukemia (AML), melanoma, renal cell cancer or a cancer that has metastasized to a lymph node.

As used herein, "sample" or "liquid samples" can refer to extracts from tissues or other biological specimens (e.g., extracts comprising proteins and metabolites) obtained by contacting tissue or biological specimen with a solvent according to the embodiments. In some aspects, a sample can be an extract from a non-biological specimen, such as the surface on an object (e.g., a forensic sample).

As used herein, "essentially free," in terms of a specified component, is used herein to mean that none of the specified components has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the terms "conduit" and "tube" are used interchangeably and refer to a structure that can be used to direct flow of a gas or liquid.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

I. The Present Embodiments

In certain aspects, the instant application provides apparatus and methods for exchanging and/or cleaning medical devices using surgical procedures. In particular embodiments, a cartridge contains medical devices that can be exchanged by changing the orientation of the cartridge.

An initial overview and discussion will be presented regarding features and operating principles of an apparatus comprising a cassette with sample acquisition probes. Following the apparatus overview, a discussion of specific features of exemplary sample acquisition probes will be presented.

Figure 1:
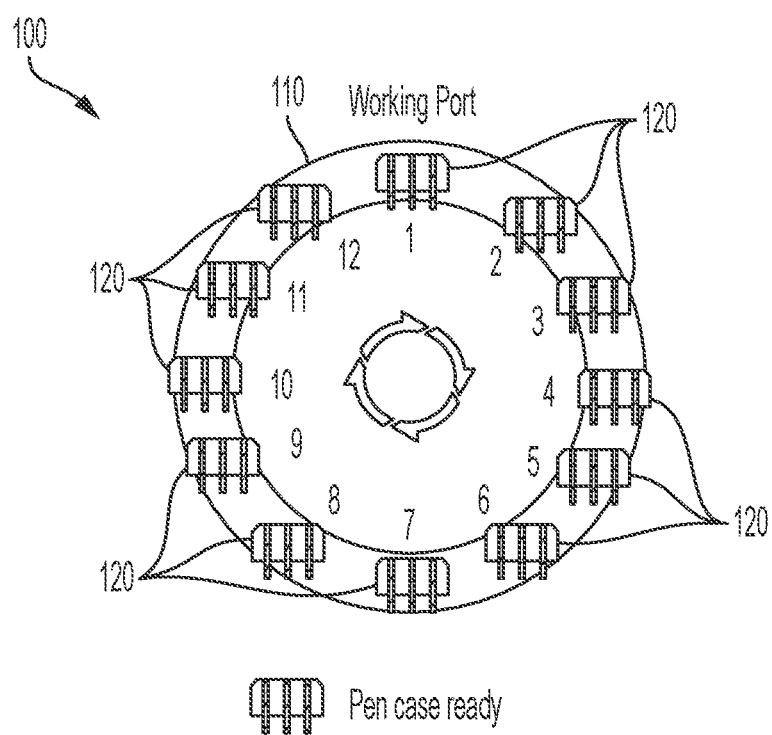
FIG. 1: Representative schematic of a front view of an apparatus for exchanging medical devices.
Figure 2:
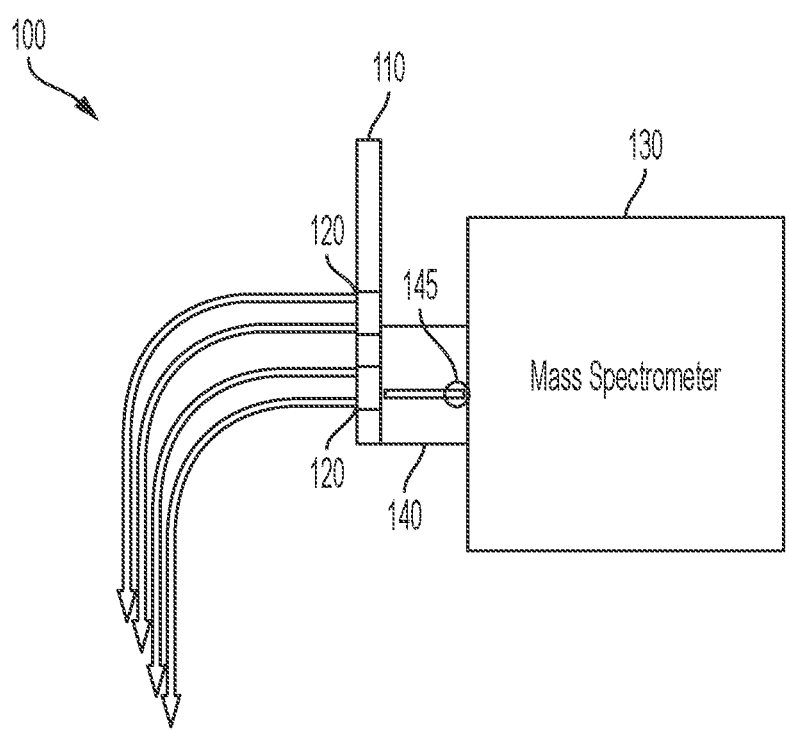
FIG. 2: Representative schematic of a side view of an apparatus for exchanging medical devices

Referring initially to FIG. 1, a front schematic view is shown of an apparatus 100 comprising a cassette 110 further comprising a plurality of sample acquisition probes 120. In this embodiment, cassette 110 is configured to rotate in a clockwise direction. FIG. 2 illustrates a side schematic view of an alternate configuration of apparatus 100 that moves linearly rather than rotates. It is understood that the present disclosure includes both embodiments and the principles of operation of each embodiment are equivalent. Accordingly, aspects of rotating components can be equally applied to linearly translating components, and vice versa.

Cassette 110 is coupled to a sample processing instrument 130 via a coupling mechanism 140. Apparatus 100 is configured such that one of the sample acquisition probes 120 is in fluid communication with a sample processing instrument 130 while the remaining sample acquisition probes 120 remain ready for use. During use, apparatus 100 allows medical personnel to quickly and efficiently switch between the sample acquisition probes 120. The ability can to switch to a different probe for each sample acquisition can reduce cross-contamination between different samples acquired and delivered to analysis instrument 130. In particular embodiments, sample processing instrument 130 may be a mass spectrometer, while in other embodiments sample processing instrument 130 may be any instrument suitable for processing a sample, including for example analyzing or storing the sample.

Coupling mechanism 140 couples a sample acquisition conduit 180 to sample processing instrument 130 to allow a sample acquired by a sample acquisition probe 120 to be processed. Coupling mechanism 140 is configured to couple an individual conduit 180 via any suitable manner that allows for de-coupling and coupling of sample acquisition conduits 180 when the orientation of cassette 110 is changed. In one embodiment, coupling mechanism 140 may include a flexible seal 145 that engages a sample acquisition conduit 180 (in fluid communication with a first probe 120) so that the sample acquisition conduit 180 is in fluid communication with sample processing instrument 130 when cassette 110 is in a particular orientation. As the orientation of the cassette 110 is changed, flexible seal 145 can disengage such that the conduit 180 is no longer in fluid communication with sample processing instrument 130. As the orientation of cassette 110 is further changed, a different sample acquisition conduit 180 (in fluid communication with a second probe 120) is engages flexible seal 145 such that the sample acquisition conduit 180 is in fluid communication with sample processing instrument 130. In certain embodiments flexible seal 145 may be elastomer or other suitable polymer.

Figure 3:
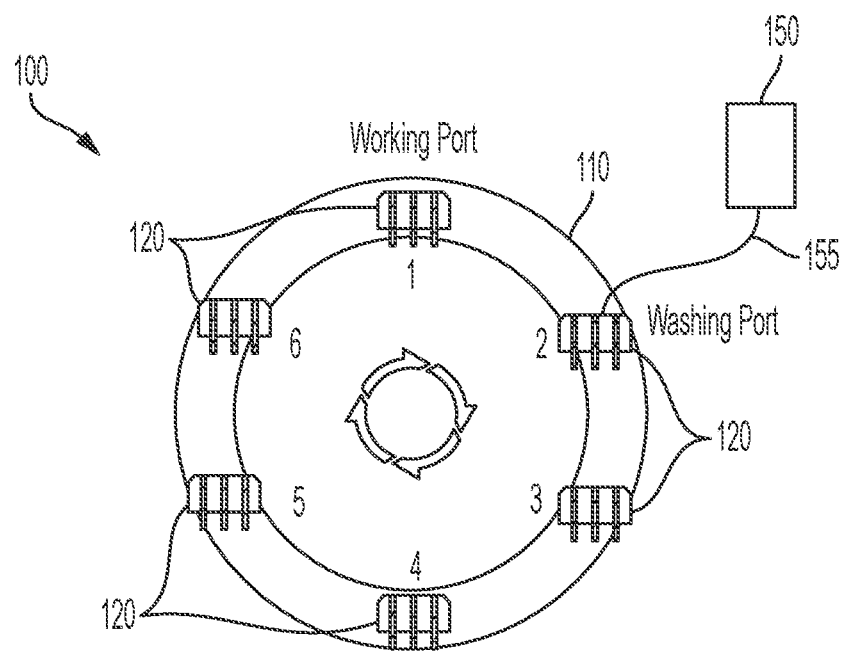
FIG. 3: Representative schematic of a front view of an apparatus for exchanging medical devices in a first position.
Figure 4:
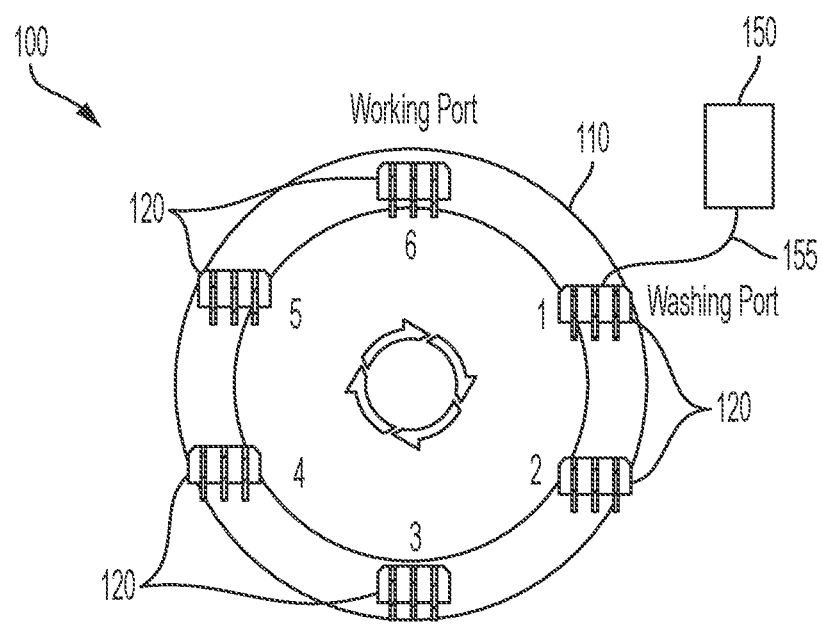
FIG. 4: Representative schematic of a front view of an apparatus for exchanging medical devices in a second position.

Referring now to FIGS. 3 and 4, another embodiment of an apparatus 100 includes the capability to wash a sample acquisition probe 120 after use. This embodiment includes a chamber 150 in fluid communication with a sample acquisition probe 120 via a conduit 155. Chamber 150 comprises a cleaning fluid that can be directed to a sample acquisition probe 120 via conduit 155 in order to clean the probe after it has been used. Cassette 110 can then be rotated to provide a clean sample acquisition probe 120 for each sample procedure. In the embodiment shown, sample acquisition probe 120 in location 1 at the top of FIG. 3 is originally designated as the working port in fluid communication with a sample processing instrument (e.g. mass spectrometer). As a result, sample acquisition probe 120 in location 1 can be used to acquire a sample and deliver it to the sample processing instrument. After the sample has been obtained and delivered to the sample processing instrument, cassette 110 can then be rotated clockwise as shown in FIG. 4.

Accordingly, sample acquisition probe 120 in location 6 is now at the working port location and can be used to acquire and deliver a different sample to the sample processing instrument. Sample acquisition probe 120 in location 1 is now in fluid communication with chamber 150 and can be cleaned. Cleaning fluid from chamber 150 can be directed through sample acquisition probe 120 to remove any material that remains from the previous sample acquisition procedure. This provides a clean sample acquisition probe 120 for subsequent procedures using the sample acquisition probe 120 in location 1 as cassette 110 is rotated.

After sample acquisition probe 120 in location 1 is cleaned, cassette 110 can then be rotated to as needed to acquire multiple samples. When sample acquisition probe 120 in location 1 is returned to the top working port location, the probe will be cleansed of potential contamination that could affect subsequent sample acquisitions with the probe.

Figure 5A:
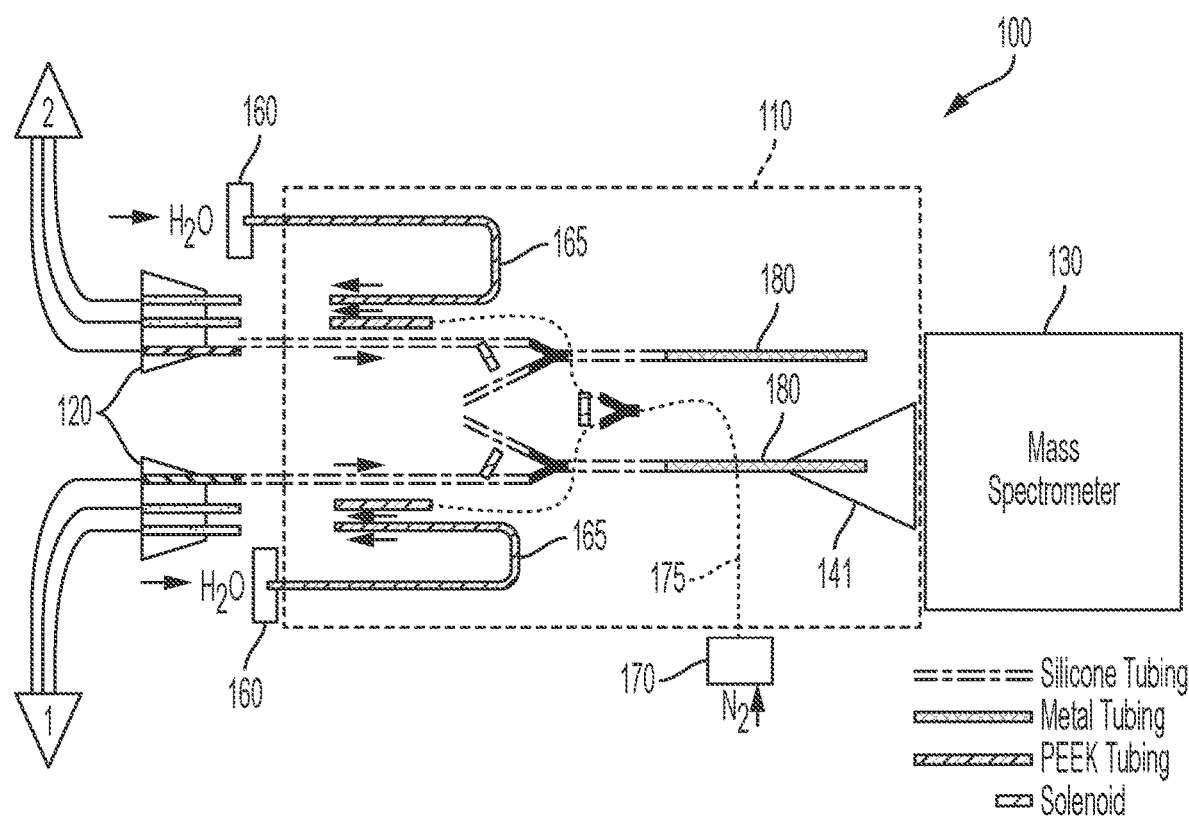
FIG. 5A: Representative schematic of a top view of an apparatus for exchanging medical devices.

Referring now to FIG. 5A, a schematic view is shown of apparatus 100, including a plurality of conduits between sample acquisition probes 120 and sample processing instrument 130 and additional components. In this embodiment, apparatus 100 does not include a rotating or translating cassette of sample acquisition probes. Instead, there are two sample acquisition probes 120. One sample acquisition probe 120 is used sample acquisition and analysis while the other probe is replaced with a clean probe. In this embodiment, apparatus 100 includes one or more chambers 160 comprising a solvent, including for example, water or another fluid (delivered via a solvent supply conduit 165) suitable for use in sample acquisition. In addition, apparatus 100 comprises a gas supply 170 and conduit 175. During use, solvent from chamber 160 and gas from gas supply 170 can be directed through a sample acquisition probe 120 to assist in acquiring a sample from a sample site.

In this embodiment, apparatus 100 comprises a first plurality of sample acquisition conduits 180, and each sample acquisition probe 120 is coupled to a conduit of the first plurality of conduits 180. Furthermore, each conduit of the first plurality of sample acquisition conduits 180 is configured to place sample processing instrument 130 in fluid communication with a specific sample acquisition probe 120 that is currently being used for sample acquisition and analysis. After one sample is acquired and directed to processing instrument 130 with a first sample acquisition probe 120, sample acquisition conduit 180 can be de-coupled from processing instrument 130. Sample acquisition conduit 180 for the second sample acquisition probe 120 can then be coupled to processing instrument 130 and a second sample can be acquired with the second sample acquisition probe 120. In certain embodiments, sample acquisition conduit 180 and processing instrument 130 can be coupled via coupling mechanism 141. In particular embodiments, coupling mechanism 141 is a quick release coupling mechanism. As used herein, a quick release coupling mechanism is defined as a mechanism that allows for coupling and de-coupling of components without the use of external tools. Accordingly, in exemplary embodiments, sample acquisition conduit 180 and processing instrument 130 can be coupled and de-coupled via coupling mechanism 141 in an efficient manner (e.g. less than five seconds) without the need to use external tools to perform the coupling and de-coupling process. In specific embodiments, coupling mechanism 141 may comprise a friction fit to couple and seal conduit sample acquisition 180 to processing instrument 130. In other embodiments, coupling mechanism 141 may comprise a Luer Lock to couple and seal conduit 180 to processing instrument 130.

While the second sample acquisition probe 120 is used to acquire a sample, a third sample acquisition probe 120 (e.g. a new probe or a probe that has been previously cleaned) with sample acquisition conduit 180 can be readied for use. After the second sample is acquired, sample acquisition conduit 180 for the second probe is removed from processing instrument 130, and a sample acquisition conduit 180 coupled to a third sample acquisition probe 120 can be coupled to processing instrument 130. A third sample can then be obtained while a fourth probe 120 and sample acquisition conduit 180 is readied for use. The process can then be repeated to allow a different sample acquisition probe 120 to be used for each sample. This procedure allows the sample acquisition process to proceed efficiently because a clean, uncontaminated sample acquisition probe 120 and sample acquisition conduit 180 is ready for use after each sample is acquired.

Apparatus 100 further comprises solenoid valves (not labeled in FIG. 5A for purposes of clarity) to restrict or allow flow of fluids through the various conduits. The solenoid valves can be controlled to allow solvent (e.g. water) to flow through the conduit when apparatus 100 is being used to acquire and analyze a sample. When processing instrument 130 is in standby mode, the solenoid valves can be positioned to restrict the solvent flow and allow air to flow to processing instrument 130. A control system can be utilized to control operation of the solenoid valves and fluid flow through the conduits.

Figure 5B:
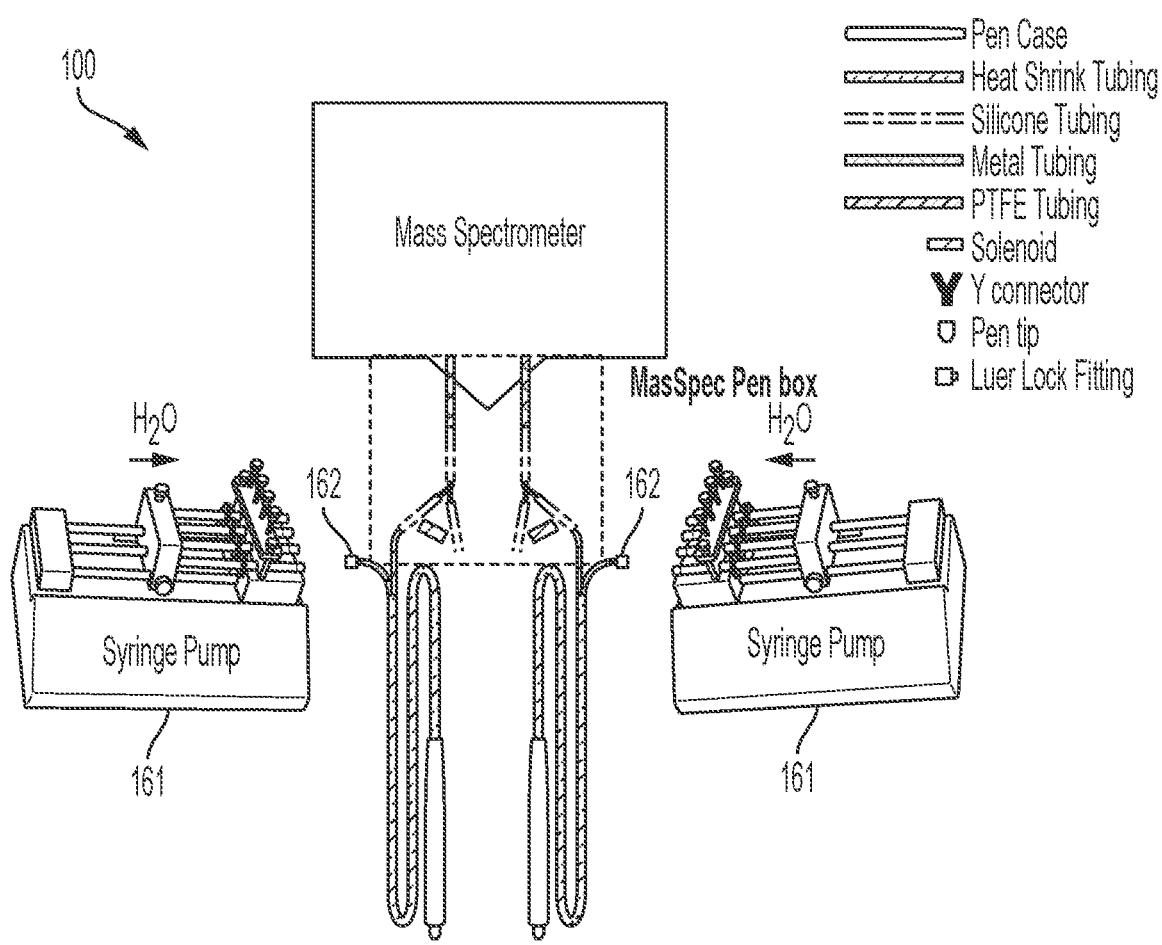
FIG. 5B: Representative schematic of a top view of one embodiment of an apparatus for exchanging medical devices.
Figure 5C:
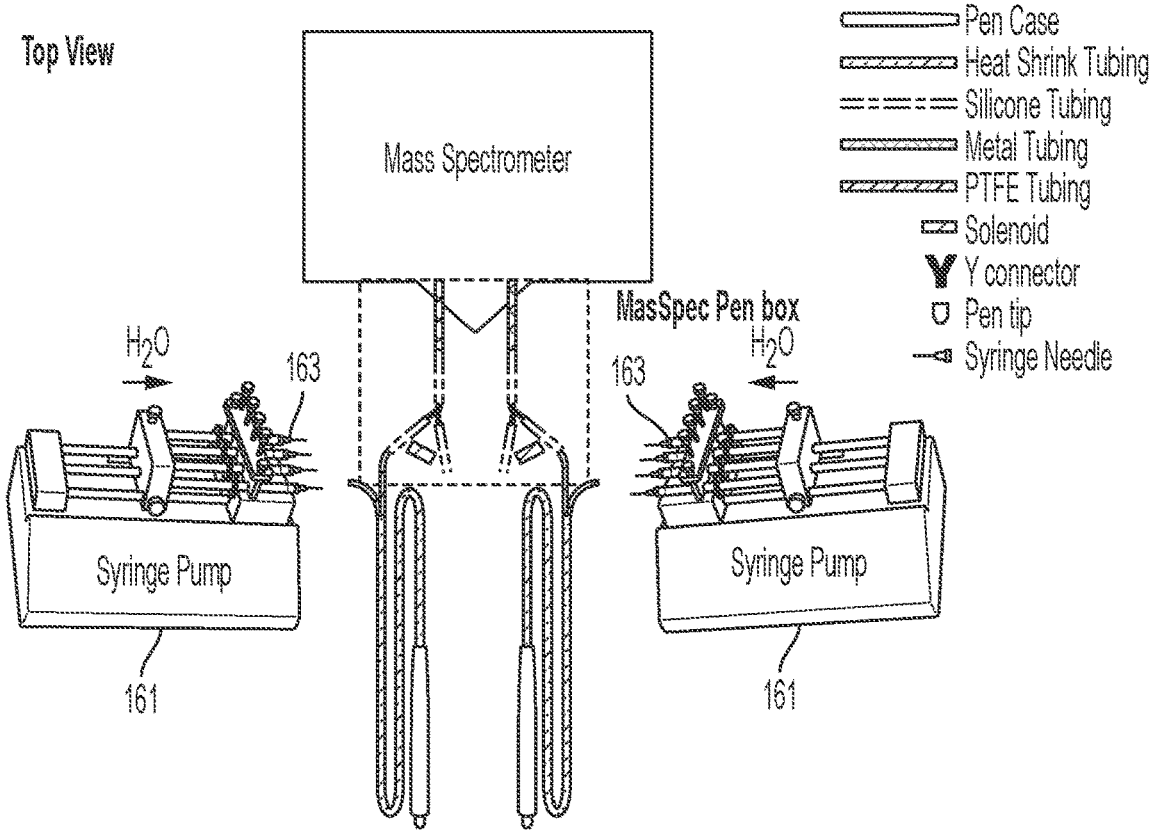
FIG. 5C: Representative schematic of a top view of a second embodiment of an apparatus for exchanging medical devices.
Figure 5D:
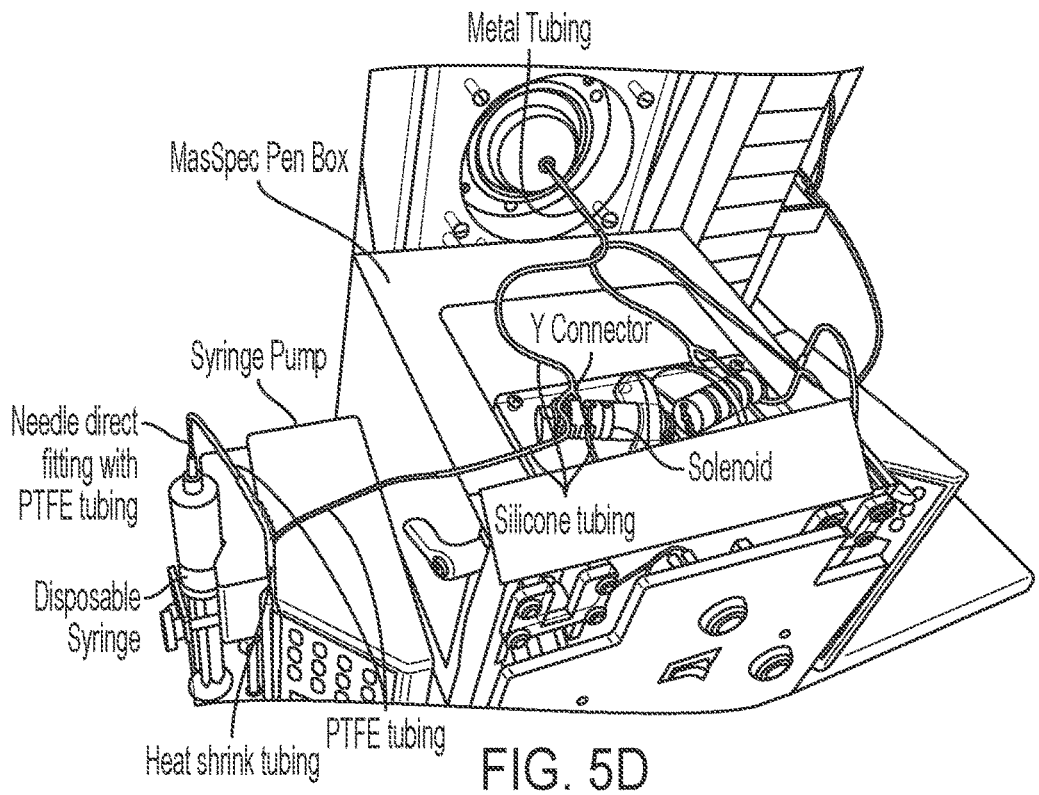
FIG. 5D: Photographic representation of a top view of one embodiment of an apparatus for exchanging medical devices during use.
Figure 5E:
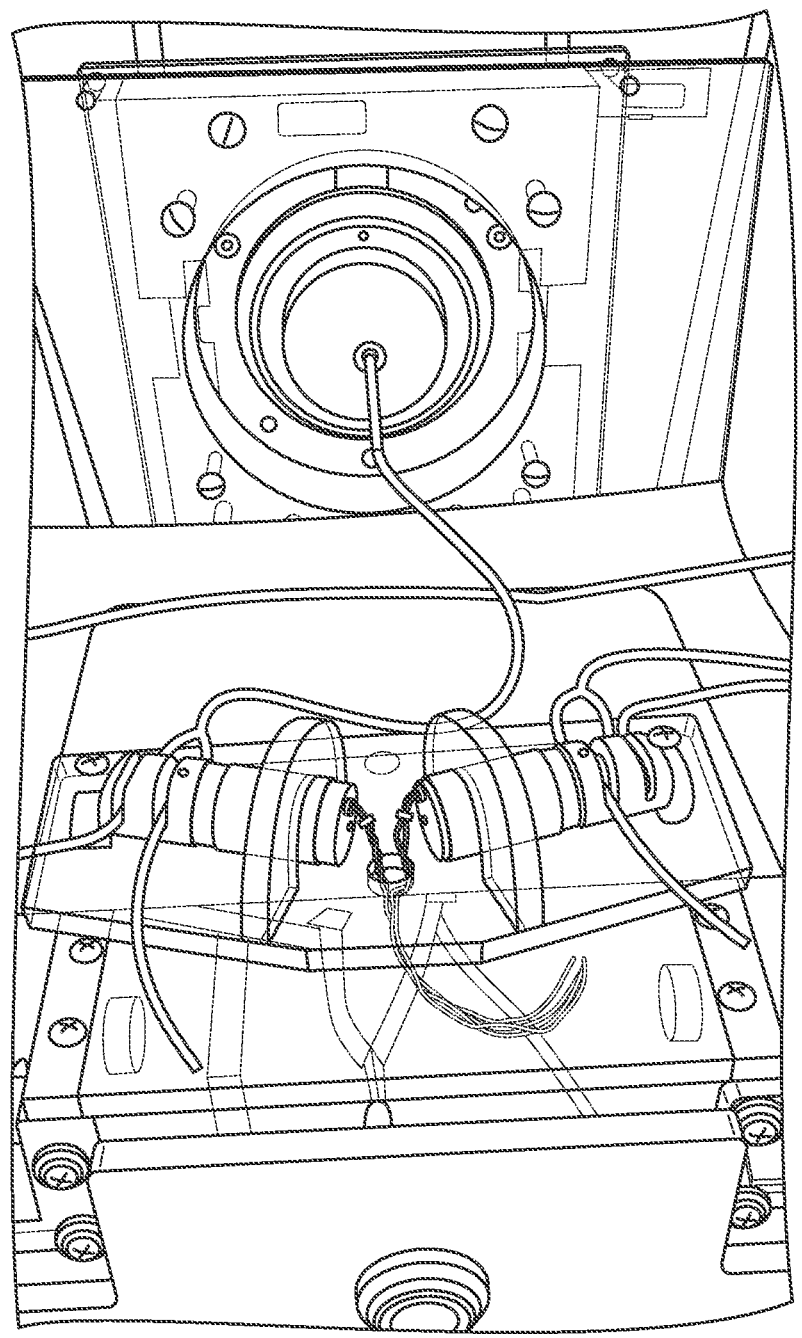
FIG. 5E: Photographic representation of a top view of the embodiment of FIG. 5D.

Referring now to FIG. 5B, a schematic view is shown of apparatus 100 in which syringe pumps 161 with Luer Lock fittings 162 are used to couple to the conduits and provide solvent flow. FIG. 5C shows and embodiment similar to that of FIG. 5B, but syringe pumps 161 utilize a needle fitting 163 to couple to the conduits and provide solvent flow. FIGS. 5D and 5E provide photographs of an apparatus 100 similar to FIG. C during use. The embodiment shown in FIGS. 5D and 5E incorporate a needle fitting providing fluid flow from the syringe activated by the syringe pump. The solenoid valves control fluid flow during sample acquisition as previously described.

The apparatus and methods shown and described above in relation to FIGS. 1-5 allow for efficiently exchanging and/or cleaning instruments during surgical procedures, including sample acquisition and assessment procedures. While the specific embodiments shown and described are directed to sample acquisition and assessment procedures, it is understood that the scope of the invention is not limited to such procedures. Embodiments of the present disclosure include other surgical procedures that include multiple steps in which biological tissues (or other matter) contacts medical devices and the chance for cross-contamination between procedural steps exists.

While the present disclosure is not limited to embodiments incorporating tissue sample probes and procedures, a more detailed discussion of such embodiments is provided in the following discussion. In certain aspects, the instant application provides methods and devices for minimally invasive molecular assessment of samples, such as tissue samples. In particular, aspects the methods can be used to assess multiple tissue sites during an operation (or biopsy) of the tissue. This feature allows for accurate identification of diseased tissues (e.g., tissue sites retaining cancer cells) in "real-time" allowing surgeons to more accurately address only the diseased tissue relative to surrounding normal tissues. In particular aspects, the methods disclosed here can involve delivery of a fixed or discrete volume of solvent to a tissue site, followed by collection of a liquid sample from the site and analysis of the liquid sample by mass spectrometry. Importantly, rather than being applied in a high-pressure spray, solvent is applied as discrete droplets and at low pressure. These methods allow for accurate collection of samples from a distinct tissue site while avoiding damage to the tissue being assessed. The resulting mass spectrometry profile from collected samples allows for differentiation of diseased versus normal tissue sites. The method can be repeated at multiple sites of interest to very accurately map molecular changes (e.g., in a tissue). Importantly, the profiles of samples could be differentiated even without the use of an ionization source. Thus, while methods of the embodiments could be used in conjunction with an ionization source, the use of such a source is not required. These methodologies can allow assessment of plurality of tissue sites over a short range of time, thereby allowing for very accurate assessment of the boundaries of diseased versus normal tissues.

In some aspects, the methods detailed herein can be used to collect and analyze samples from a wide range of sources. For example, the methods can be used to assess surgical, forensic, agriculture, pharmaceutical, and/or oil/petroleum samples.

In some aspects, the materials (PDMS and PTFE) and solvent (e.g., water only solvents) used in the devices of the embodiments are biologically compatible, such that they can be used in surgery in for real-time analysis. Furthermore, because the devices can be very compact, it can be hand-held and used in used in minimally invasive surgical procedures, or non-surgical procedures.

In some aspects, the present invention provides devices of extended length and increased compactness for delivery of fixed or discrete volumes of solvents to tissues for use in minimally invasive surgeries. In some aspects, these methods can be encapsulated in a variety of form factors such as a conduit, ranging from 0.5 mm to 10.0 mm inner diameter (e.g., with an inner diameter of between about 1.0 and 5.0; 1.0 and 10.0; 2.0 and 8.0; or 5.0 and 10.0 mm). In some aspects, the site of delivery of a fixed or discrete volume of solvent, followed by collection of a liquid sample may be inside the body, such as a surgical site. In some aspects, two smaller conduits may be inserted into a third, larger, conduit to create a multi-lumen catheter. For example, the multi-lumen catheter can have 2, 3, 4, 5, 6 or more luminal spaces with each having an internal diameter of, e.g., 0.05 to 5.0 mm; 0.1 to 5.0 mm; 0.25 to 3.0 mm; or 0.5 mm to 10.0 mm. The multi-lumen catheter may be attached to a mass spectrometry device for analysis of sample tissues inside the body during surgery, while avoiding unnecessary damage to surrounding tissues.

In some aspects, the device may be used through cannulas or catheters in minimally invasive surgical or endoscopy procedures, or may be used in non-surgical procedures through needle guides or biopsy guides. In some aspects, the present invention can be integrated into a robotic surgical system allowing several regions of the human body cavity to be quickly sampled and analyzed. In some aspects, the device be used to analyze tissues using a database of molecular signatures and machine learning algorithms, allowing diagnosis in real time for each sampled region. The present invention may be used in a wide variety of oncological and other surgical interventions, such as endometriosis, for which real time characterization and diagnosis of tissues are needed.

In some aspects, the present disclosure provides an attachment to the probe, for fine manipulation of the probe during minimally or non-invasive procedures. For example, the attachment to the probe may be a fin. In some aspects, the present invention may further comprise a device for grasping the probe, external to the probe, in order to manipulate the probe during laparoscopic procedures. The grasping device may be used to hold, rotate, or move the probe, or may grasp the fin attached to the probe, in order to move or rotate the probe.

In some aspects, the present invention maintains a reservoir using a multi-lumen catheter with recessed ports for depositing water and nitrogen gas during laparoscopic surgical procedures. A multi-lumen catheter may be formed, for example, using a multi-lumen extrusion as is well known in the art. These catheters may be utilized in any cannula. The most commonly used cannulas are of 5 mm and 10 mm diameters, and are typically used for laparoscopic surgeries.

In some aspects, the present disclosure provides tools, devices and methods for manipulation of the probe during endoscopy. For example, multi-lumen tubing may be used with an external vacuum source in order to attach the probe to the tissue surface while analyzing.

In some aspects, the present invention provides a shutter system that occludes the orifice of the minimally invasive surgical device. In some aspects, this shutter system may be a catheter balloon that is integrated within the device or added separately to the device. The shutter, or balloon, may close the probe tip, preventing unwanted biological material from entering the device, including the lumens and tubing, upon insertion of the catheter into the patient. The shutter or balloon may disallow endogenous biological fluids from entering the mass spectrometer after analysis has been initiated, thus preventing contamination of the results. Finally, closing of the shutter or balloon may prevent excess nitrogen gas and water from entering the body. Inclusion of lengthened probes for minimally invasive surgeries and occlusion technologies for the tips of the probes may mitigate the unpredictable and often tumultuous nature of internal organ movement and organ systems during surgery which could affect signal acquisition. Balloons technologies could also be used in other region of the device instead or in addition to the pinch valves to control solvent and gas motions through the tubes.

In some aspects, the present invention may be used with robotic manipulation. In some aspects, the technologies of the present invention may integrate in modern surgical theaters through an accessory port, or via a robotic arm. These devices may be integrated into robotic systems such as the Intuitive Surgical da Vinci robotic surgical system. A device of the present invention may have its own dedicated arm in a robotic system, or be handled by robotic graspers by incorporating a "fin" onto the probe. Smaller and larger diameters can also be used to be coupled to any existing catheters, cannulas and also needle/biopsy guides.

In some aspects, a tracking probe can be integrated with this device in order to display and record where the tissue sample has been analyzed to better assist the surgeon in localizing the sampling points both intraoperatively or otherwise. For example, during intraoperative ultrasound, an ultrasound emitter on the device may be utilized to display the probe when sampling. The probe may be integrated with a tracking device based on radio frequency technology, such as the Biosense Webster Carto system. In that case, the probe may display the device/sampling location on any of a variety of imaging modalities, such as intraoperative UltraSound (US)/Computed Tomogrpahy (CT)/Magnetic Resonance Imaging (MRI)/Optical Coherence Tomography (OCT). Additionally, fluorescent imaging and molecular dyes may be used to track the analyzed areas and charted to provide 2-dimensional or 3-dimensional spatial imaging. More simply, the probe tip may be coated with a surgical dye which is then stamped on the tissue to track the region analyzed. Yet another tracking approach is to integrate an RF emitter into the probe so that the spatial location may be tracked.

In some aspects, the probe of the present invention may be used to assist surgeons and medical professionals during minimally invasive surgical interventions by providing comprehensive and definitive diagnostic molecular information in vivo and in real time, without necessarily causing damage or alteration to the patient's native living tissues. The handheld MasSpec Pen has demonstrated a capacity to do this during non-laparoscopic/endoscopic surgical procedures (U.S. patent application Ser. No. 15/692,167 incorporated herein by reference, in its entirety). Similarly to the handheld MasSpec Pen, the present invention is suitable for ex vivo analysis of tissues (fresh, frozen, sections, biopsies) or other clinical specimens that might be examined by a pathologist, and may be used for chemical analysis of any given sample for which direct analysis is desired in confined and spatially limited domains (animals, plants, explosives, drugs, etc). A variety of tissue types may be analyzed as well, including but not limited to, breast, kidney, lymph node, thyroid, ovary, pancreatic and brain tissues.

In some aspects, the probe of the present invention may be used in conjunction with surgical instruments for the treatment of a disease. A variety of surgical instruments may be used to excise or ablate cells or tissues, including, but not limited to, laser ablation tools, tools for cauterization or electrocauterization, or tools for the manual dissection of tissue such as a scalpel.

Thus, many regions of the human body cavity can be quickly sampled during surgery, and analyzed (e.g., by using a database of molecular signatures and machine learning algorithms). Therefore, the diagnostic results may be provided in real time for each sampled region. Exemplary devices for use in these methods are detailed below.

II. Exemplary Features of a Device of the Embodiments

A. Shutter Systems

In some aspects a device of the embodiments further comprises a shutter system that can occlude the orifice, and creates a separation between the reservoir and the tissue. For example, the shutter system can activate after the droplet rests for 3 seconds and before the droplet is transported to the mass spectrometer. One reason for this is to ensure no biological material reach the mass spectrometer and cause damage to the instrument. The shutter can be an iris diaphragm, a mechanical closure, gate, or tapenade. An additional design for the shutter is a balloon mechanism, which seals the exterior of the device from the tissue. The balloon can be positions on the distal end of the conduit, e.g., perpendicular to the pen or probe. When activated, the balloon expands and fills up the reservoir towards the direction of the tissue. This accomplishes at least 3 things: first it gently lifts the pen tip off of the tissue using the inflated balloon, insuring that there is no damage to the tissue. This is to ensure that the probe remains nondestructive and biocompatible in case the analyzed tissue is determined to be 'normal'. Secondly, it seals the solvent droplet that is inside the reservoir and prevents leakage or absorbance of lipids after the sampling window. Thirdly, it creates a seal at the end of the conduit, which will allow for more effective transfer of the droplet to the mass spectrometer.

B. Catheter Systems

In some cases, where a probe is incorporated into a laparoscopic/endoscopic device a reservoir includes using a multi-lumen catheter, e.g., with recessed ports for depositing water and nitrogen gas. The reservoir also retains the water during the extraction period. A multi-lumen catheter can be formed for example using a multi-lumen extrusion as is well known in the art. It has been demonstrated that these catheters can be utilized in any cannula, most commonly 5 mm and 10 mm diameters, for laparoscopic surgeries. This technology is compatible with robotic manipulation such as the Intuitive Surgical da Vinci robotic surgical system. The Laparoscopic/Endoscopic probes will easily integrate in current surgical theaters through an accessory port or via a robotic arm. Smaller and larger diameters can also be used to be coupled to any existing catheters, cannulas and also needle/biopsy guides.

C. Valve Systems

In further aspects, a probe system of the embodiments can incorporate additional valves. For example, micro-solenoid valves can be located at each conduit, e.g., at the distal end of the sampling probe. These will be individually controlled by an arduino, microcontroller, or signal. In some cases the value operation is automated. In other cases it can be manually controlled. In some aspects, valves are positioned in the inner wall of the solvent conduit sealing the conduits. Thus, by using such values, only two or even one conduit can be used in the sampling operation. For example, a delivering solvent conduit and a return conduit to transfer the droplet to the mass spectrometer. Additional micro-solenoids could be implanted to have more control. For example, three or four micro-solenoids can be into the probes of the embodiments.

D. Further Surgical System Features

In some aspects, medical devices require passage to areas of the body that are difficult to maintain manual control. One solution is to use endoscopic catheters, but these are often less precise when compared to handheld devices. Further control can be attained using robotic tools that can function nearly to the same extent, and sometimes better than physicians equipped with a traditional scalpel. A further feature of the Laparoscopic/Endoscopic probes of the embodiments is a 'fin' that can be grasped by forceps, robotic tools, or laparoscopic graspers. This will allow the probe to be used in a variety of modalities without sacrificing resolution or sensitivity. In some aspects, the fin itself is a gradual sloped protrusion from the exterior of the conduit running parallel to said conduit. It is textured to provide extra traction for the grasping mechanism.

In further aspects, a tracking probe can be integrated with this device in order to display and record where the tissue sample has been analyzed to better assist the surgeon in localizing the sampling points both intraoperatively or otherwise. For intraoperative ultrasound, an ultrasound emitter on the device may be utilized to display the probe when sampling. Alternatively, the probe can be integrated with a tracking device based on radio frequency technology, such as the e.g., Biosense Webster Carto system. With this approach, the probe displays the device/sampling location on any various imaging modalities like intraoperative Ultra-Sound (US)/Computed Tomography (CT)/Magnetic Resonance Imaging (MRI)/Optical Coherence Tomography (OCT).

In some further aspects, tissue sites that are assessed by a probe of the embodiments can be marked. For example, a dye that is up-taken by cancerous cells and normal cells, which will mark where the probe has been placed. In some aspects, a chemical dye can be delivered using an additional conduit in the catheter or by using a multilumen catheter. An alternative delivery of a tracking dye is to dissolve it in the solvent that we use to analyze the tissue. For instance, one advantage of using a dye within the solvent is that it will directly correlate with where the tissue sample was taken, instead of the peripheral region. Of course in this aspect, the chemical dye would be present in the mass spectra and would have to be distinguished from biomolecules in a sample. In some aspects, it may useful to make the dye visible (e.g., in white operating room light). In other aspects, the dye may be a fluorescent dye. In yet a further aspect, the pen tip can be coated with a surgical dye, which is then stamped on the tissue to track the region analyzed. Likewise, as discussed above, a tracking approach can be used to virtually map the tissues sites analyzed. For instance, a RF emitter can be integrated into a probe so that the spatial location may be tracked. Thus, in some aspects, dyes (or probe tracking) can be used to track analyzed areas of tissues. In some aspects, tissues analyzed can be charted to provide 2 dimensional and 3 dimensional spatial imaging.

In further aspects, a probe system can include a filter. For example a filter can prevent biological tissue from going into the conduits. For example, a filter mesh system can be incorporated within the device to prevent smaller bodies of tissue, protein aggregates, or coagulated cell clusters from entering. This mesh could be placed at the opening and have contact with the tissue, or be positioned higher up within the probe, such that no tissue contact occurs. In some aspects such a filter mesh comprises average aperture sizes of less than about 1.0, 0.5, 0.25 or 0.1 mm. Since solid matter can damage a mass spectrometer, such a filter system can increase instrument lifespan without negatively effecting signal detected.

In still further aspects, an endoscopic/laparoscopic probe of the embodiments is integrated with a microcontroller, user interface, and/or associated hardware that will operate with appropriate software.

In some further cases, a light, such as a LED will be incorporated to provide visual feed back to the user, for example, to indicate that the probe is ready for sampling, in the process of doing so, or needs to be replaced/repaired. Acoustic feedback can also be used, for instance, to let the user know what step of the process the device is in (e.g., since physical cues may be unavailable laparoscopically). A user interface system can also be integrated with the device, such as in a foot pedal and buttons on the housing of the probe.

III. Assay Methodologies

In some aspects, the present disclosure provides methods of determining the presence of diseased tissue (e.g., tumor tissue) or detecting a molecular signature of a biological specimen by identifying specific patterns of a mass spectrometry profile. Biological specimens for analysis can be from animals, plants or any material (living or non-living) that has been in contact with biological molecules or organisms. A biological specimen can be samples in vivo (e.g. during surgery) or ex vivo.

A profile obtained by the methods of the embodiments can correspond to, for example, proteins, metabolites, or lipids from analyzed biological specimens or tissue sites. These patterns may be determined by measuring the presence of specific ions using mass spectrometry. Some non-limiting examples of ionizations methods that can be coupled to this device include chemical ionization, laser ionization, atmospheric-pressure chemical ionization, electron ionization, fast atom bombardment, electrospray ionization, thermal ionization. Additional ionization methods include inductively coupled plasma sources, photoionization, glow discharge, field desorption, thermospray, desorption/ionization on silicon, direct analysis in real time, secondary ion mass spectroscopy, spark ionization, and thermal ionization.

In particular, the present methods may be applied or coupled to an ambient ionization source or method for obtaining the mass spectral data such as extraction ambient ionization source. Extraction ambient ionization sources are methods with, in this case, liquid extraction processes dynamically followed by ionization. Some non-limiting examples of extraction ambient ionization sources include air flow-assisted desorption electrospray ionization (AF-ADESI), direct analysis in real time (DART), desorption electrospray ionization (DESI), desorption ionization by charge exchange (DICE), electrode-assisted desorption electrospray ionization (EADESI), electrospray laser desorption ionization (ELDI), electrostatic spray ionization (ESTASI), Jet desorption electrospray ionization (JeDI), laser assisted desorption electrospray ionization (LADESI), laser desorption electrospray ionization (LDESI), matrix-assisted laser desorption electrospray ionization (MALDESI), nanospray desorption electrospray ionization (nano-DESI), or transmission mode desorption electrospray ionization (TM-DESI).

As with many mass spectrometry methods, ionization efficiency can be optimized by modifying the collection or solvent conditions such as the solvent components, the pH, the gas flow rates, the applied voltage, and other aspects which affect ionization of the sample solution. In particular, the present methods contemplate the use of a solvent or solution which is compatible with human issue. Some non-limiting examples of solvent which may be used as the ionization solvent include water, ethanol, methanol, acetonitrile, dimethylformamide, an acid, or a mixture thereof. In some embodiments, the method contemplates a mixture of acetonitrile and dimethylformamide. The amounts of acetonitrile and dimethylformamide may be varied to enhance the extraction of the analytes from the sample as well as increase the ionization and volatility of the sample. In some embodiments, the composition contains from about 5:1 (v/v) dimethylformamide:acetonitrile to about 1:5 (v/v) dimethylformamide:acetonitrile such as 1:1 (v/v) dimethylformamide:acetonitrile. However, in preferred embodiment the solvent for use according to the embodiments is a pharmaceutically acceptable solvent, such as sterile water or a buffered aqueous solution.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Minimally Invasive Probe for Mass Spectrometry Design

Figure 6:
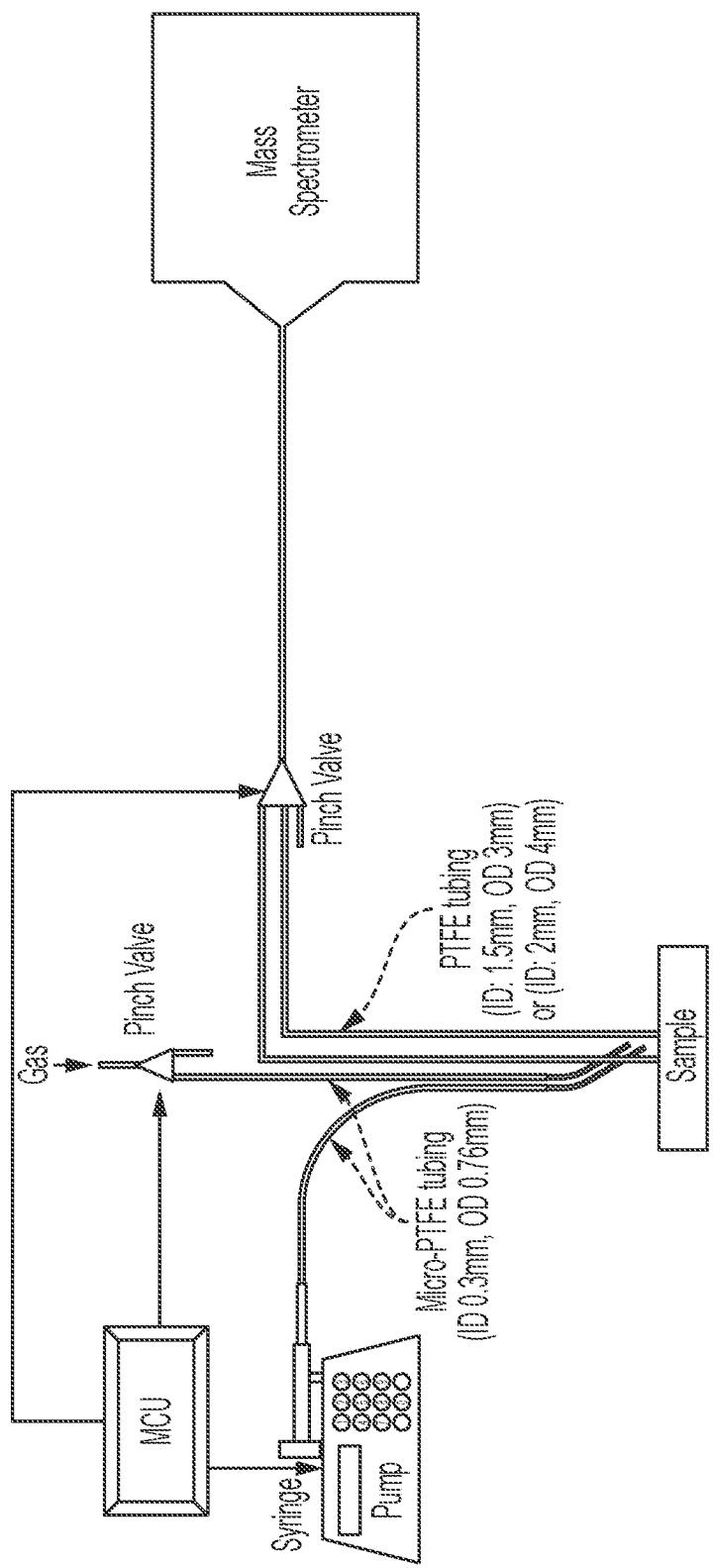
FIG. 6: Representative schematic of a mass spectroscopy probe for minimally invasive surgery.
Figure 7:
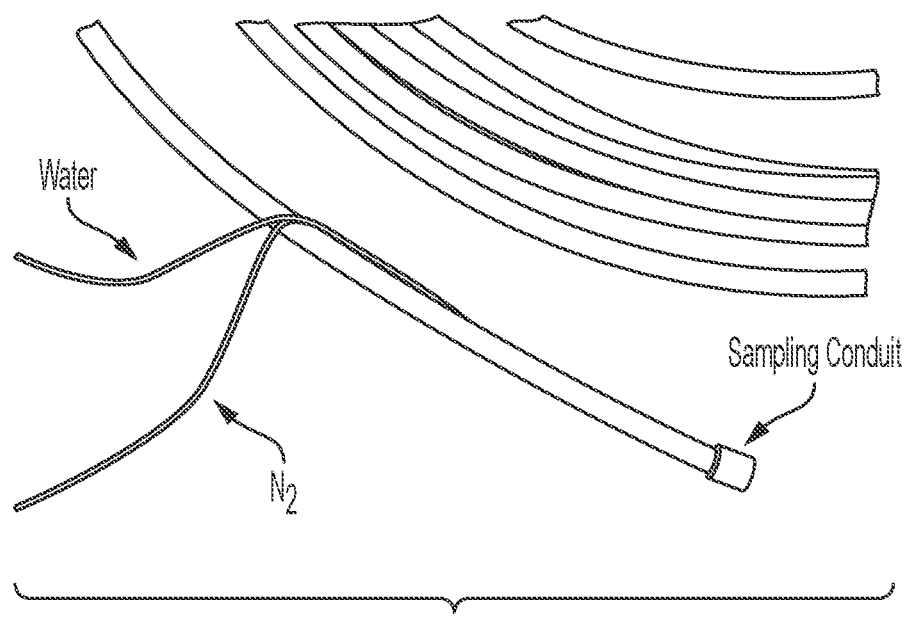
FIG. 7: Multilumen tubing for use with the mass spectroscopy probe for minimally invasive surgery.
Figure 8:
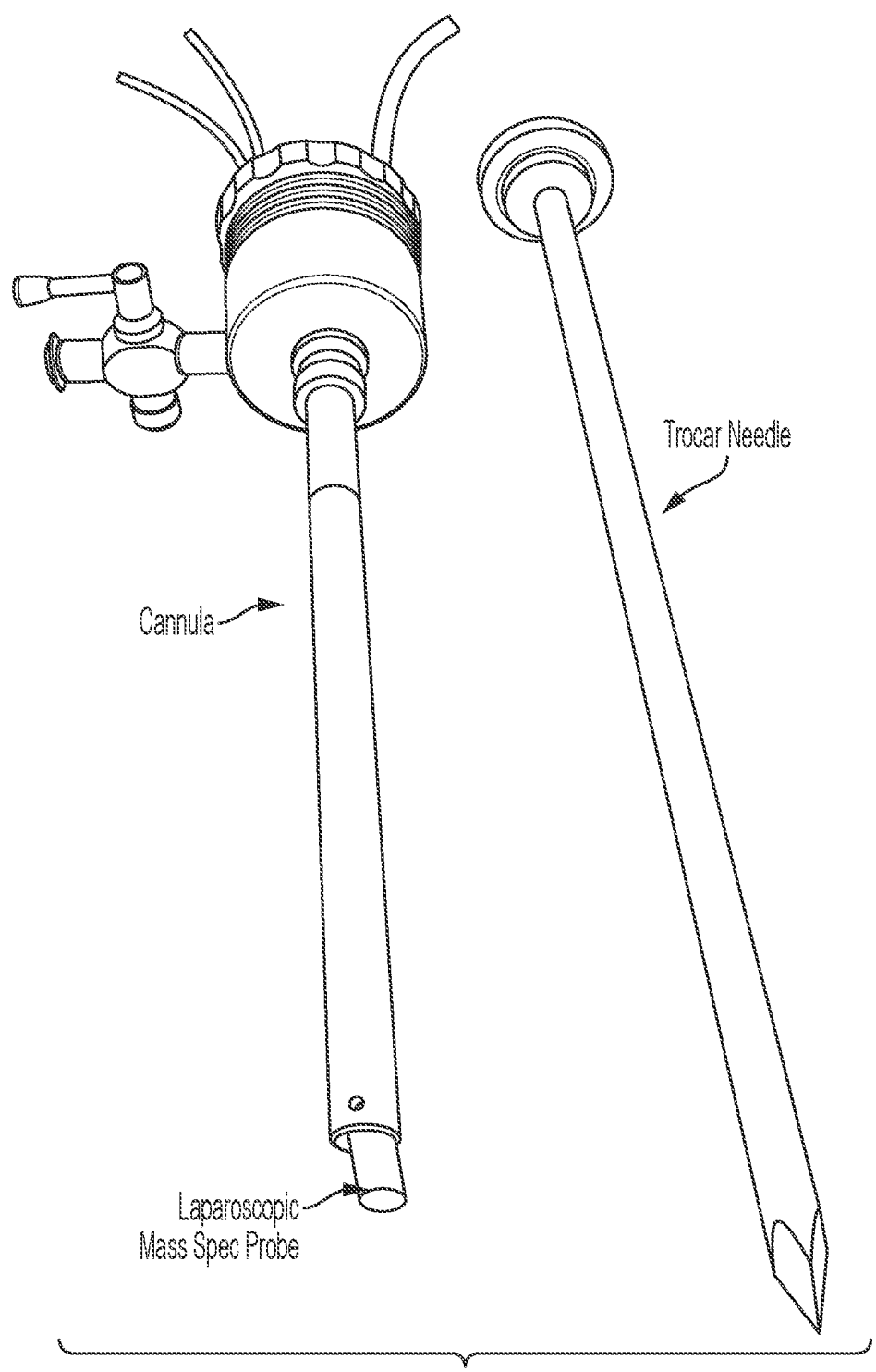
FIG. 8: A cannula and trocar needle for housing and inserting the mass spectrometry probe for minimally invasive surgery.
Figure 9:
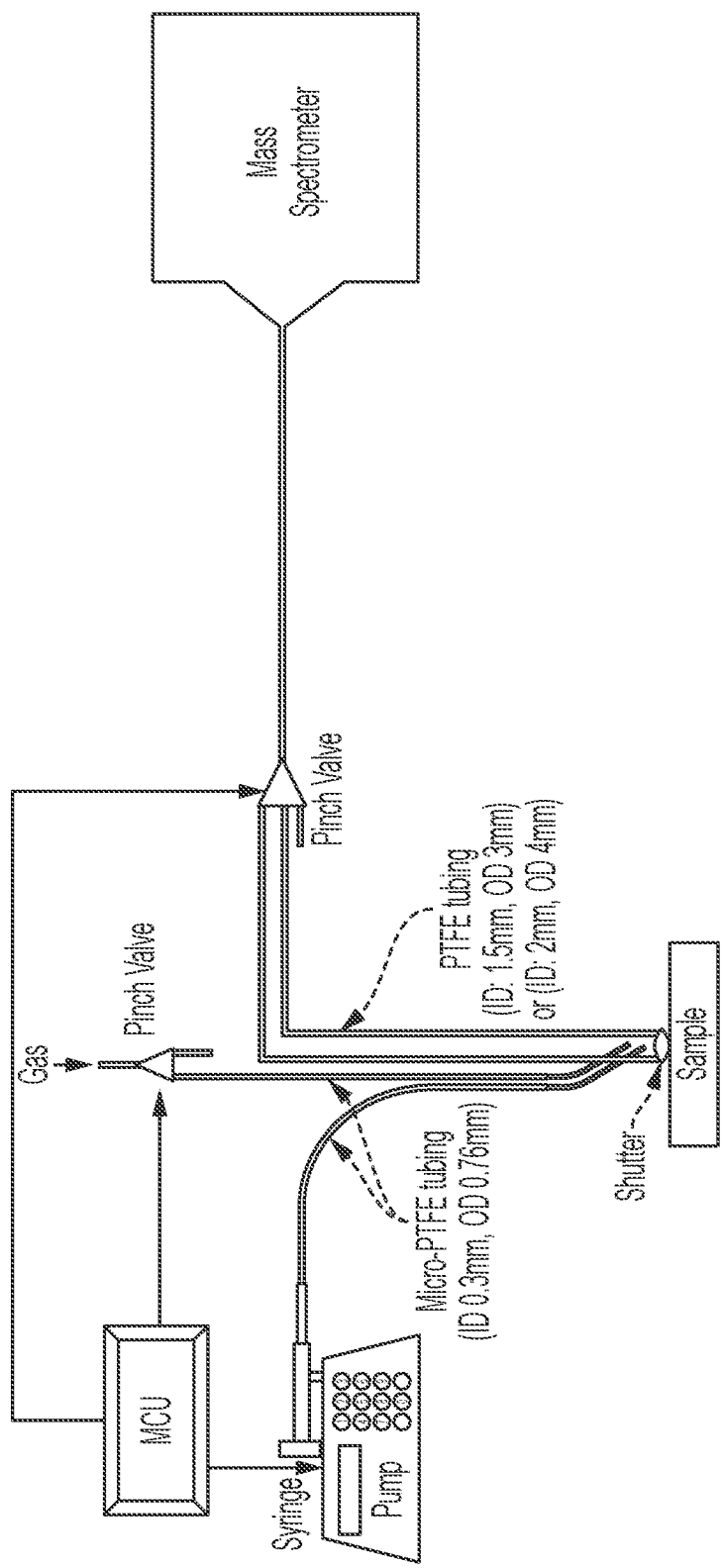
FIG. 9: Representative schematic of a mass spectrometry probe for minimally invasive surgery. This embodiment includes a shutter for occluding the probe.
Figure 10:
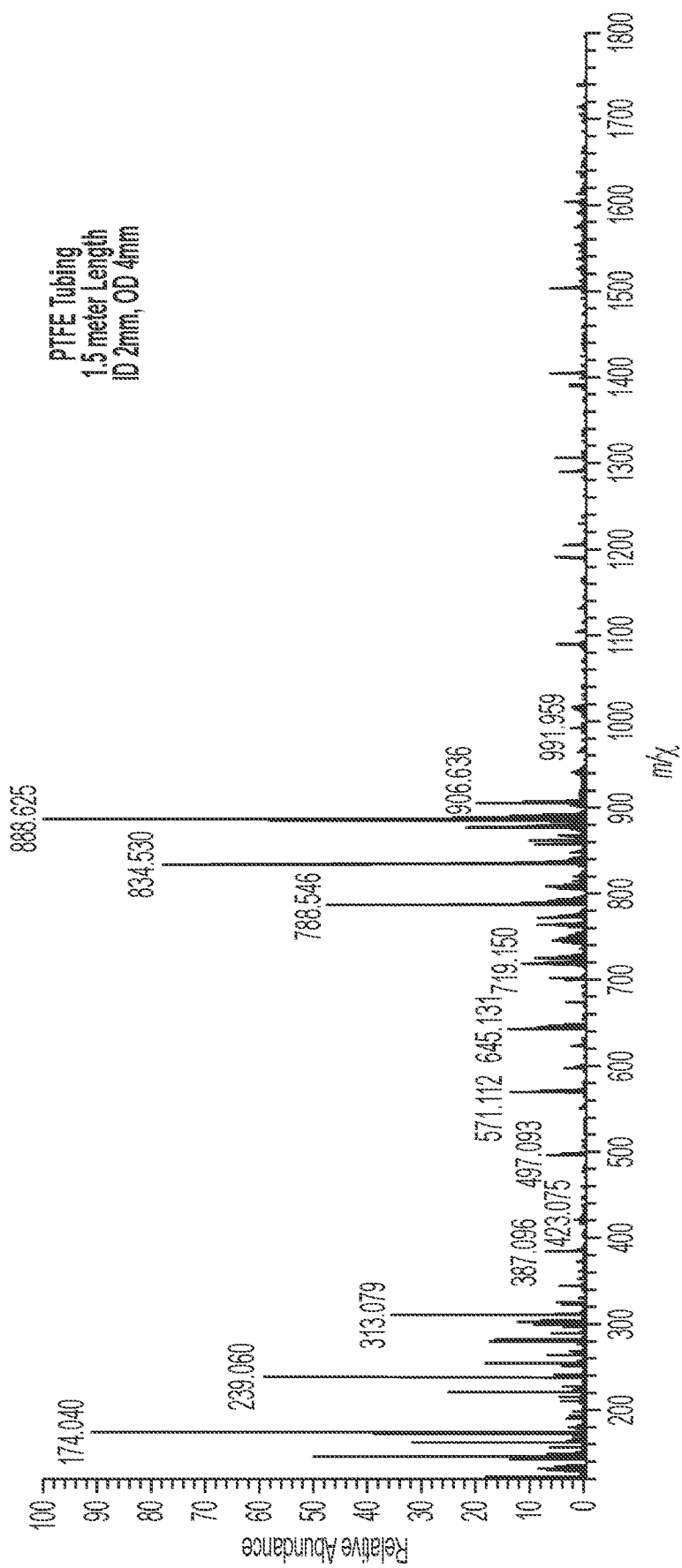
FIG. 10: Mass spectra of mouse brains tissue section from the minimally invasive mass spectrometry probe using Q Exactive Orbitrap Mass Spectrometer. PTFE tubing of 1.5 meters was used with an inner diameter of 2 mm and outer diameter of 4 mm.
Figure 11:
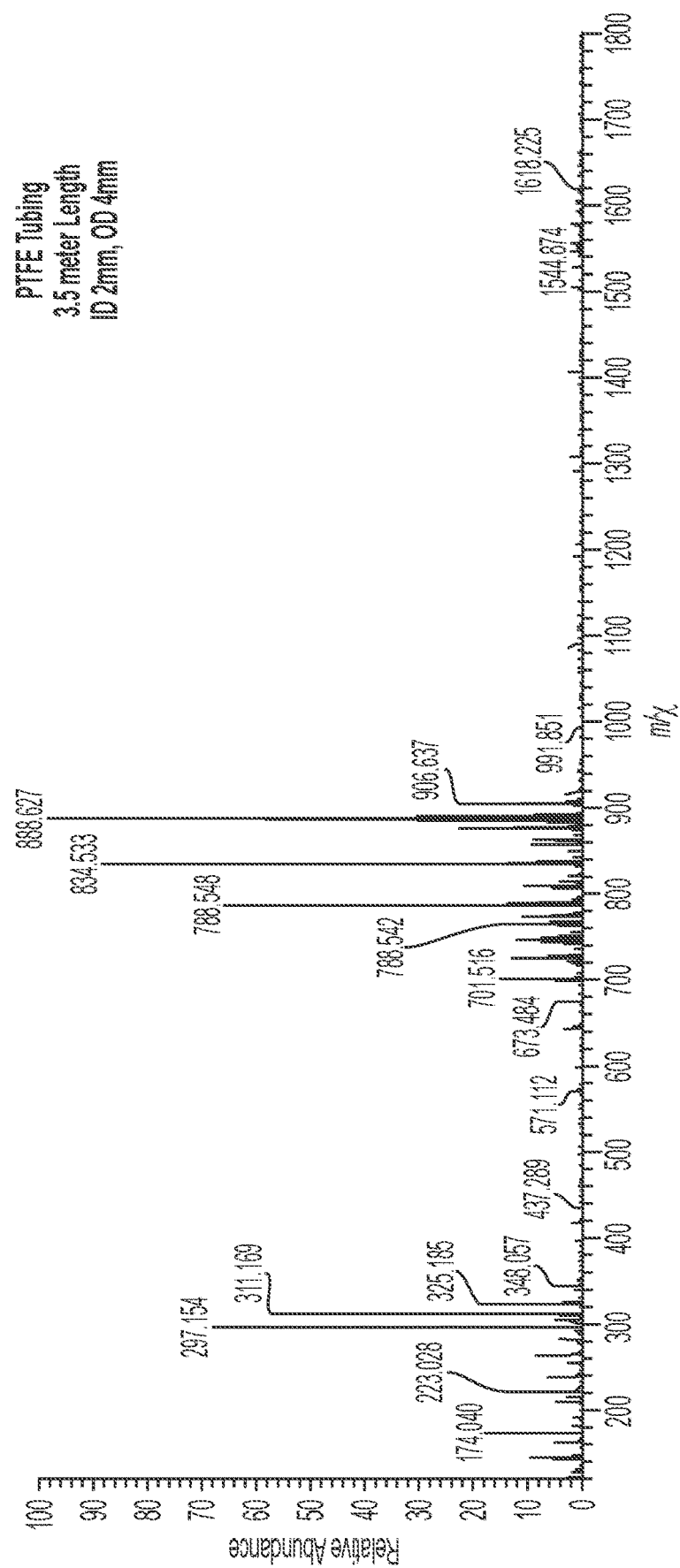
FIG. 11: Mass spectra of mouse brains tissue section from the minimally invasive mass spectrometry probe using Q Exactive Orbitrap Mass Spectrometer. PTFE tubing of 3.5 meters was used with an inner diameter of 2 mm and outer diameter of 4 mm.
Figure 12:
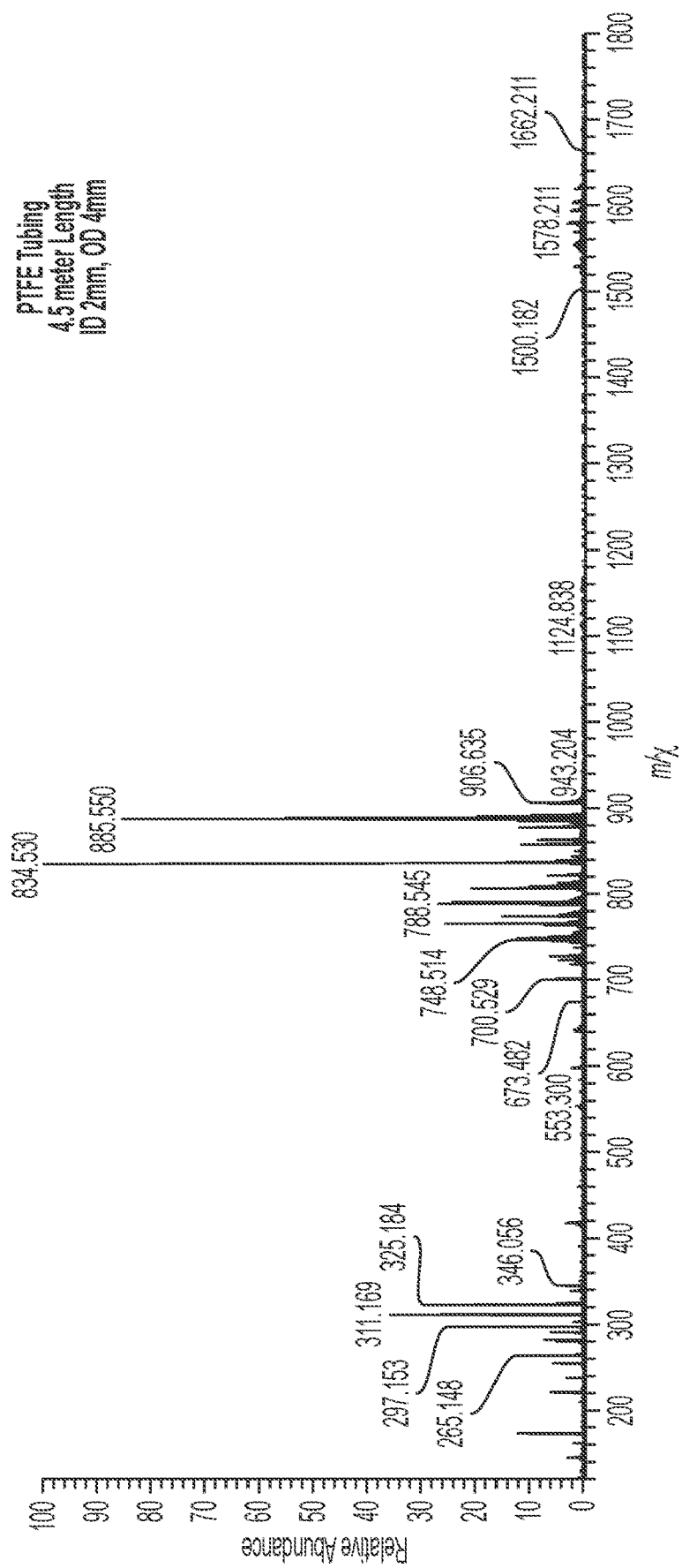
FIG. 12: Mass spectra of mouse brains tissue section from the minimally invasive mass spectrometry probe using Q Exactive Orbitrap Mass Spectrometer. PTFE tubing of 4.5 meters was used with an inner diameter of 2 mm and outer diameter of 4 mm.
Figure 13:
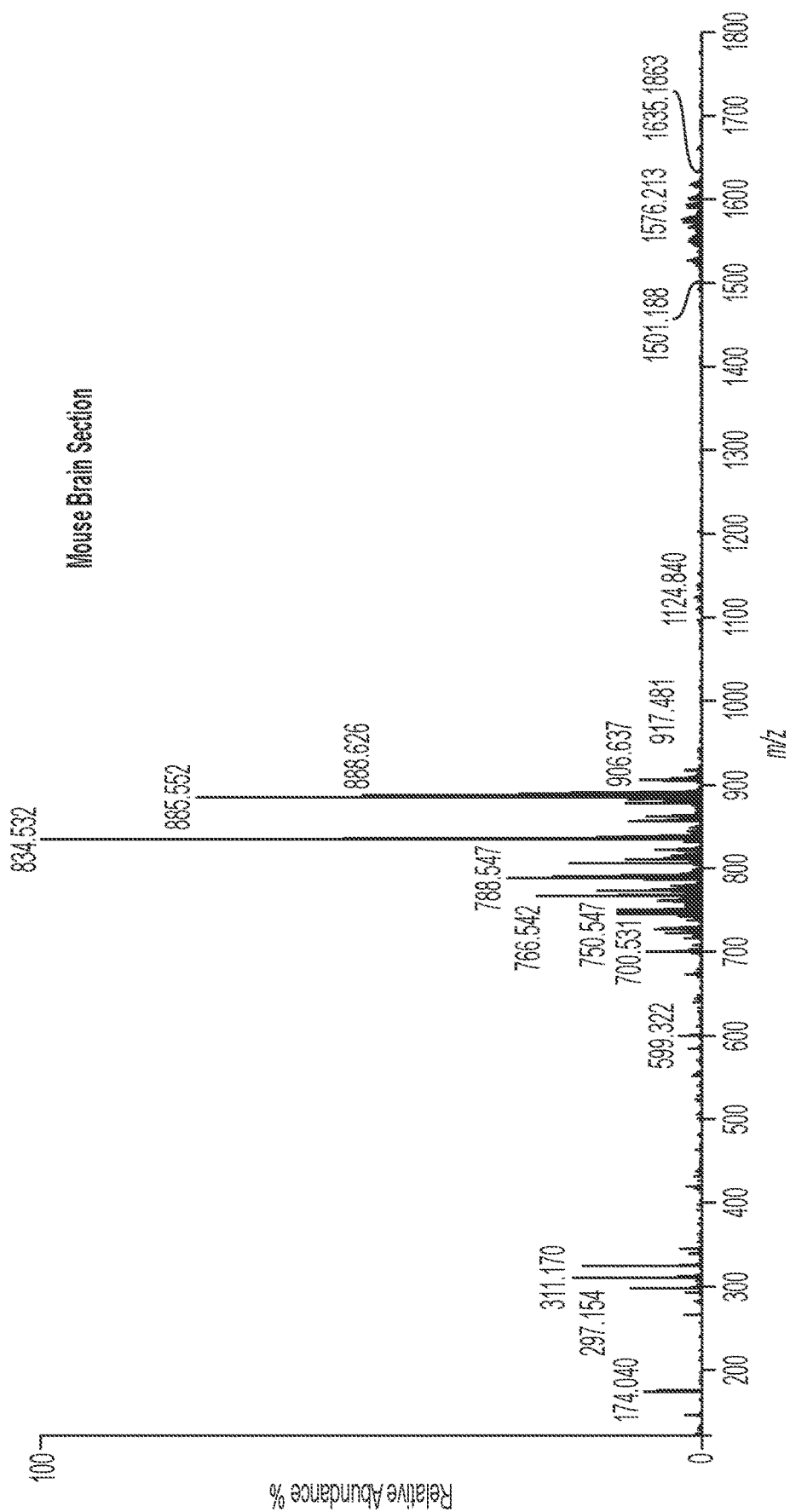
FIG. 13: Mass spectra of mouse brain tissue section from the minimally invasive mass spectrometry probe using Q Exactive Orbitrap Mass Spectrometer.
Figure 14:
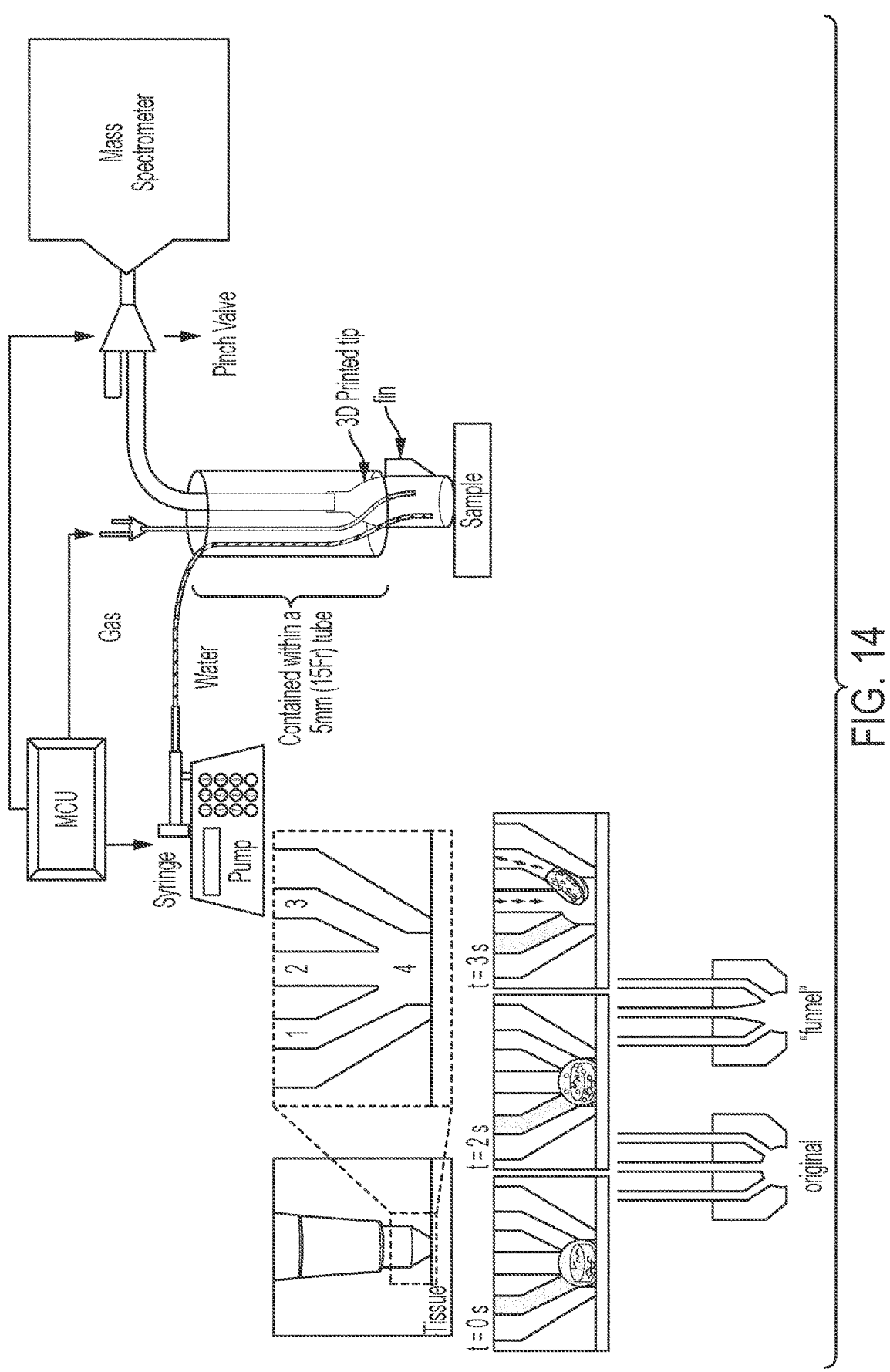
FIG. 14: Representative schematic of a mass spectrometry probe for minimally invasive surgery. Depicted on the lower left is the multichannel probe tip.
Figure 15:
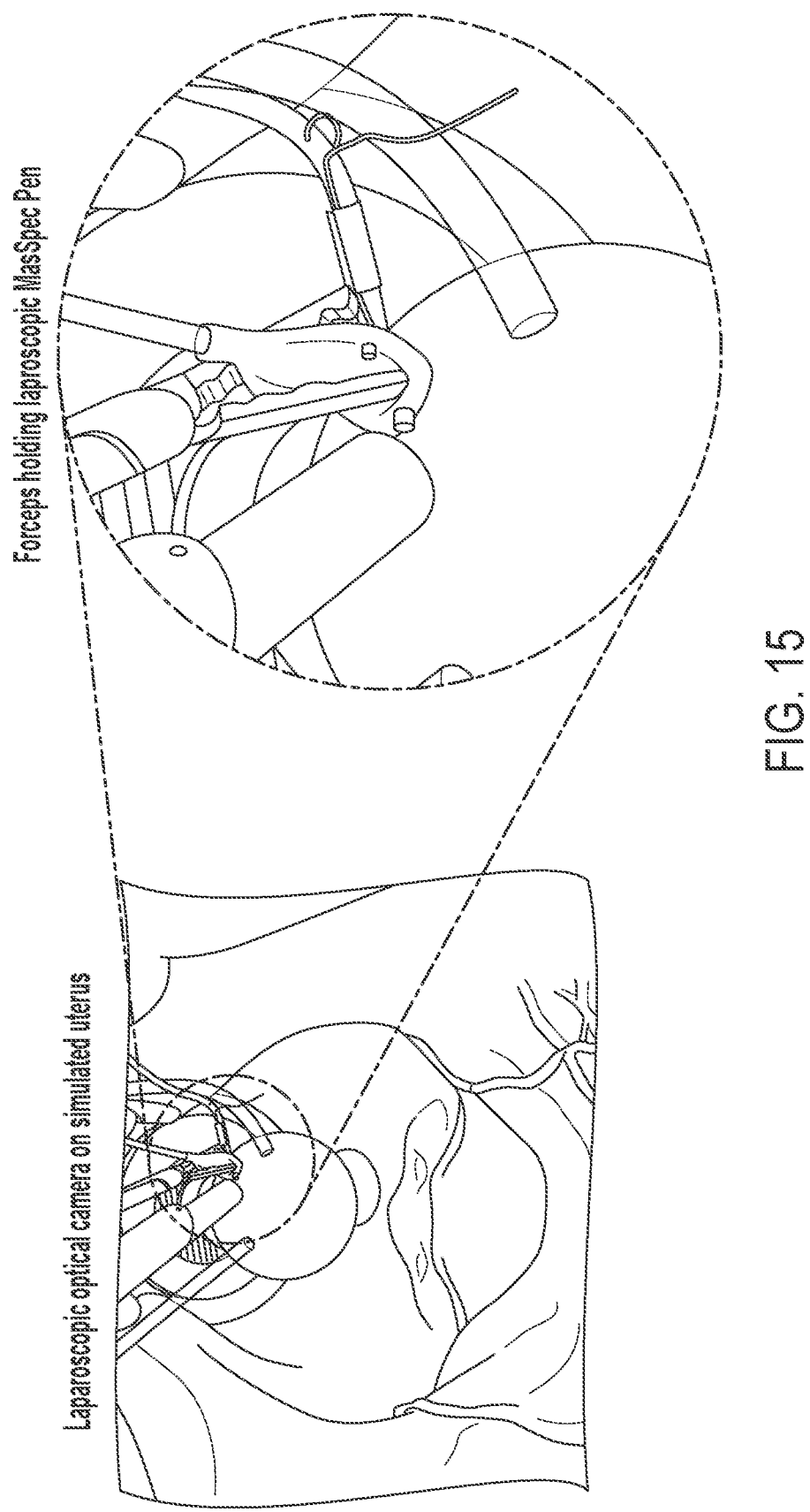
FIG. 15: Simulated laparoscopic surgery shown from a laparoscopic optical camera on a simulated uterus. Shown on the right are forceps holding the minimally invasive mass spectrometry probe.
Figure 18:
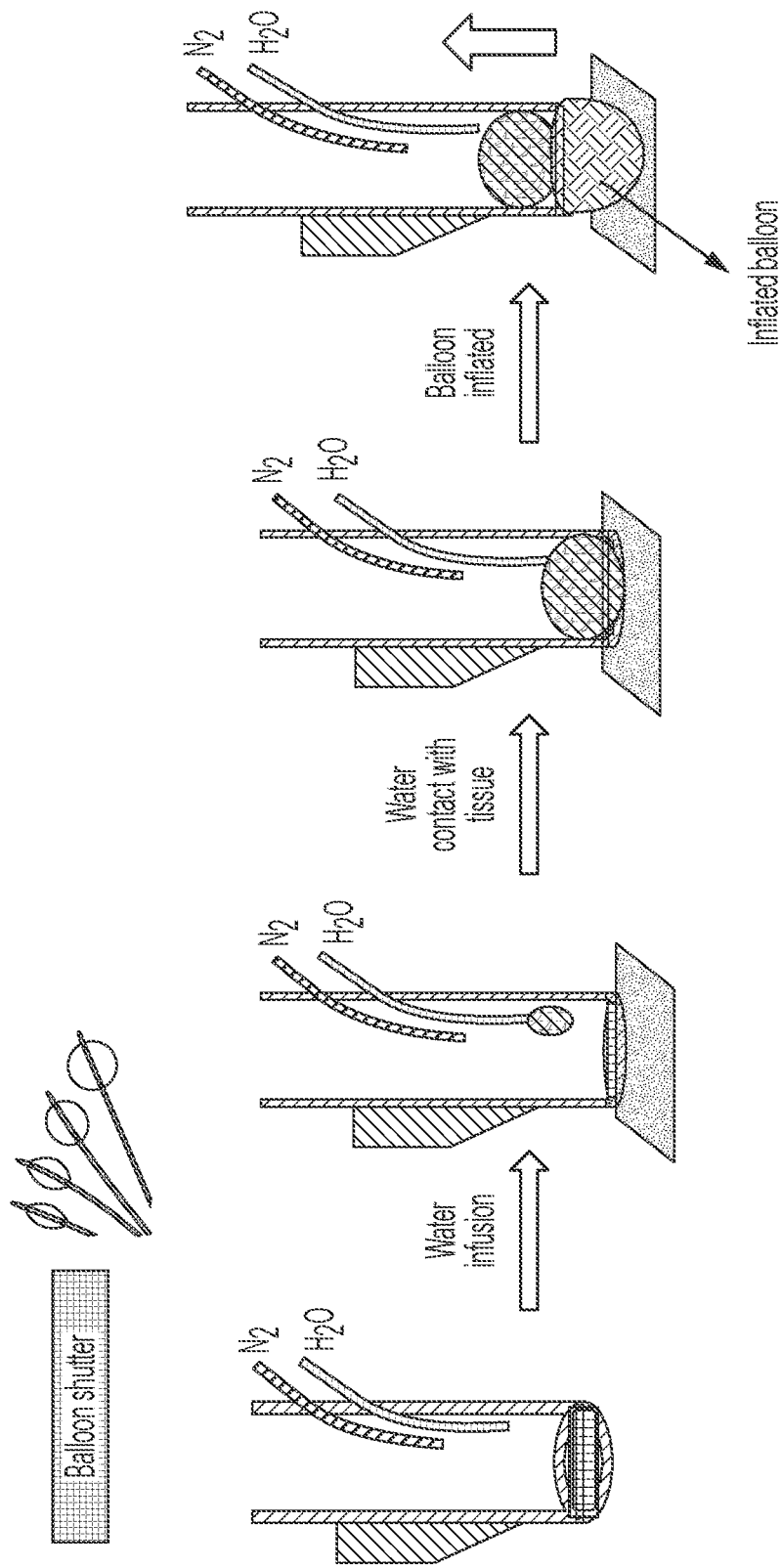
FIG. 18: Depiction of the mechanics of a balloon shutter for use with the minimally invasive mass spectrometry probe.

The system developed consists of three main parts: 1) a syringe pump that is programmed to deliver a discrete solvent volume using a controlled flow rate; 2) tubing systems integrated to two-way pinch valves for controlled solvent and gas transport; 3) a probe tip which is used for direct sampling of biological tissues. The tubing systems and probe tip are also integrated into a minimally invasive surgical device such as a cannula or catheter for use in laparoscopic or endoscopic surgeries. Several iterations of the system were explored and optimized with the ultimate goal of minimizing tissue damage, maximizing tissue-analyte extraction, and maximizing solvent transmission to the mass spectrometer. FIG. 6 shows a schematic figure of one example of a minimally invasive apparatus for analyzing biological tissue. The syringe pump feeds solvent and gas into the minimally invasive probe via micro-PTFE tubing. The probe maintains contact with the sample, retains solvent during interaction with the tissue. The tip was manufactured using 3D-printing and is made of biologically compatible polydimethylsiloxane (PDMS). The probe has three main ports: one for the incoming tubing system, a central port for gas delivery, and a third for the outgoing tubing system. All ports come in junction at a small reservoir where the droplet is retained and exposed to the tissue sample for a controlled amount of time, allowing for efficient extraction of molecules. The size of the reservoir determines the spatial resolution of the device. A solvent volume of 10 µL is exposed to the tissue sample. FIG. 7 shows the three conduit tubes. The three conduit tubes used are made of polytetrafluoroethylene (PTFE), which is also biologically compatible. The tube from the syringe pump is used to deliver solvent from syringe pump to the probe tip, while the other micro-PTFE tube is used to deliver an inert gas ($N_2$ or $CO_2$) to the probe tip. The gas serves three main purposes: 1) tissue drying prior to analysis; 2) prevent solvent gap due to the mass spectrometer's vacuum when the reservoir is closed by contacting the tissue specimen; 2) assist solvent transport from tissue to the mass spectrometer through the wider PTFE tubing. The larger PTFE tubing is directly connected to the inlet of the mass spectrometer so that the positive pressure of the mass spectrometer vacuum system is used to drive the droplet from the reservoir to the mass spectrometer inlet for ionization. FIG. 14 shows a schematic of the minimally invasive probe which includes a diagram of the tip of the probe in the lower left portion of the figure, including the three conduit tubes and the reservoir at the base (labelled 4). In certain embodiments, the middle conduit tube may comprise a funnel-shaped (e.g. tapered) chamber near the reservoir such that the larger end of the funnel-shaped chamber is proximal to the reservoir and the smaller end of the tapered chamber is distal from the reservoir. FIG. 8 shows two of the possible devices to house the minimally invasive probe. The cannula shown has the gas and solvent tubing entering the top, as well as the tubing to the mass spectrometer. The probe is shown emerging from the bottom of the cannula. The probe may also be introduced into the body cavity using a trocar needle. FIG. 15 depicts a simulated laparoscopic uterine surgery, and shows that the minimally invasive probe may be controlled by forceps. A shutter system that occludes the orifice of the minimally invasive probe may be employed as shown in FIG. 9. One option for the shutter is to use a catheter balloon which may close the probe tip, a diagram of which is shown in FIG. 18, preventing unwanted biological material from entering the device, including the lumens and tubing, upon insertion of the catheter into the patient. The shutter may disallow endogenous biological fluids from entering the mass spectrometer after analysis has been initiated, thus preventing contamination of the results. Closing of the shutter can also prevent excess nitrogen gas and water from entering the body. The use of a shutter in the lengthened probes necessary for minimally invasive surgery may help mitigate the unpredictable and often tumultuous nature of internal organ movement and organ systems during surgery which could affect signal acquisition. The minimally invasive mass spectrometry probe may also include a vacuum tube separate from the sample vacuum above. The purpose of this second vacuum tube is to gently secure, or latch, the tip of the probe onto the tissue during analysis.

The time events involved in the device operation are automated and precisely controlled by software that communicates with an Arduino system and two two-way pinch valves. All pinch valves are closed until the process is initiated when, under 300 µL/min, a pulse is sent to the pump to infuse the solvent for two seconds and stop, generating a 10 µL droplet filling in the minimally invasive probe reservoir. The gas and mass spectrometer tubes are closed at pinch valves, allowing the solvent in the reservoir to interact with the tissue for three seconds to extract the molecules. The pinch valves controlling the gas and mass spectrometer tubes are opened simultaneously, allowing the droplet to transfer to the mass spectrometer for ionization and molecular analysis. A pulse is sent to the pump to infuse the solvent for another 12 seconds and stop, to completely drive all the extracted molecules into the mass spectrometer. The gas and mass spectrometer tubes are left open for another 20 seconds to allow all the solvent in the mass spectrometer tube to go into the mass spectrometer. The total analyzing time is 37 seconds.

Figure 20:
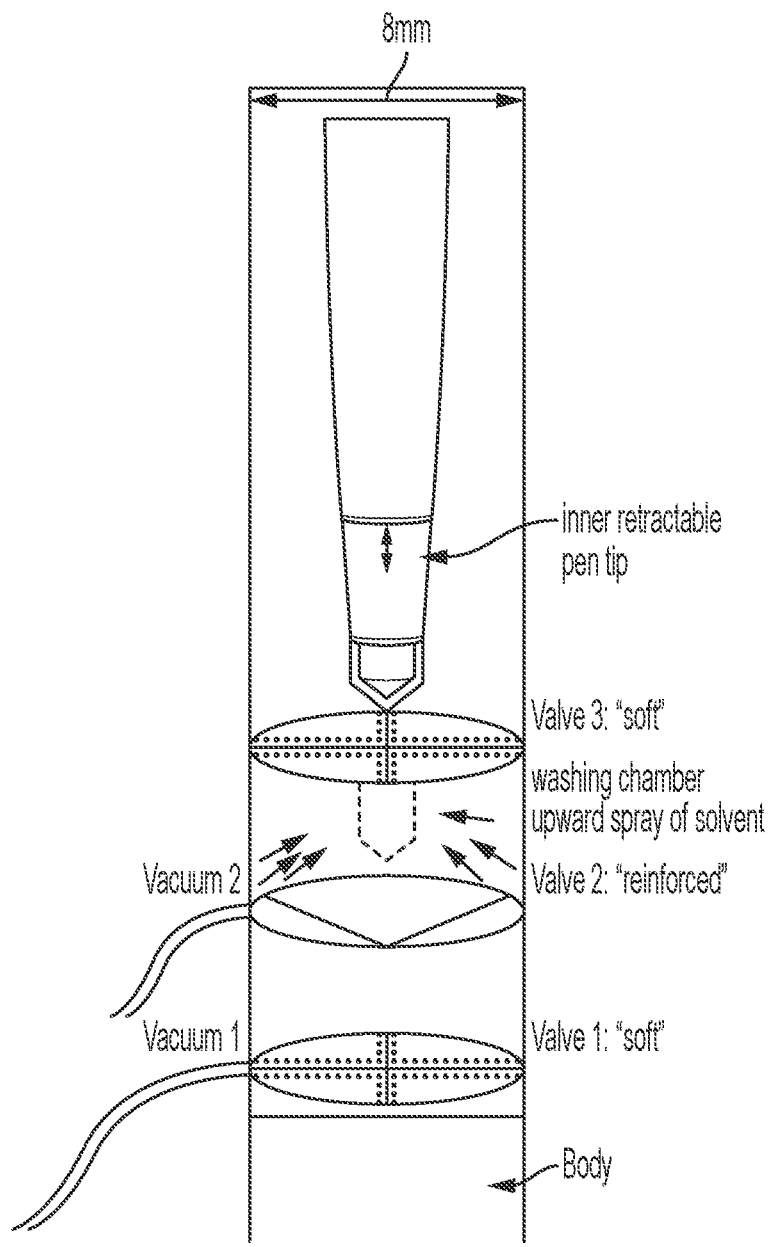
FIG. 20: Diagram of washing chamber for minimally invasive mass spectrometry probe.

The probe may be washed between analyses in a variety of methods. Generally, the tip of the probe is wiped with sterile water. An additional design that can facilitate the washing step is a retractable design that will wash the exterior of the probe without having to remove the device from the patient (FIG. 20). The design consists of a chamber with valves located at the openings to maintain a water and gas seal. A longer tube that contains the probe tip, water, and gas conduits will transect only the top valve when the tip is located in the washing chamber, but will pass through both valves when the tip is deployed into the patient environment. After the probe tip, tubing, or both have become contaminated during the surgery process, the probe will withdraw into the washing chamber. Water tubes can be located inside the washing chamber and point upwards providing a strong jet of cleaning solvent. Two positions of vacuum tubing will be located above the first and second valve to remove dirtied solvent. The vacuum tube placed above the first valve is an emergency tube in case any water breaks the first valve barrier. The entire system will fit smoothly inside of a trocar, and the deployable probe will be located inside of this system. The vacuums located inside the probe will also operate during this cleaning process, which will flush the tubing until clean.

Example 2

Molecular Profiles and Analysis

The system described herein operates by directly connecting the transfer tube to the mass spectrometer inlet for transporting the analyte-containing solvents to the mass spectrometer for molecular analysis. This set up greatly simplifies operational details and precludes the use of ionization sources. After the probe interacts with the tissue, the solvent is then transported to the mass spectrometer and directly infused without the need of an additional ionization source. Since the system is fully automated so that each 10 µL solvent droplet is delivered separately to the inlet, the mass spectrometer operates without any impact on its performance. Rich molecular information is obtained in this manner, similar to what is observed from other solvent-extraction ambient ionization techniques such as desorption electrospray ionization. The ionization mechanism may be similar to inlet ionization. For inlet ionization methods, the ionization occurs in the inlet pressure drop region between atmosphere and vacuum. Because of the nature of minimally invasive surgical techniques, the diameter of tubing, and length of tubing is of critical importance. A variety of tube lengths were tested for the delivery of solvent to the mass spectrometer, as seen in FIGS. 10-13).

Figure 16:
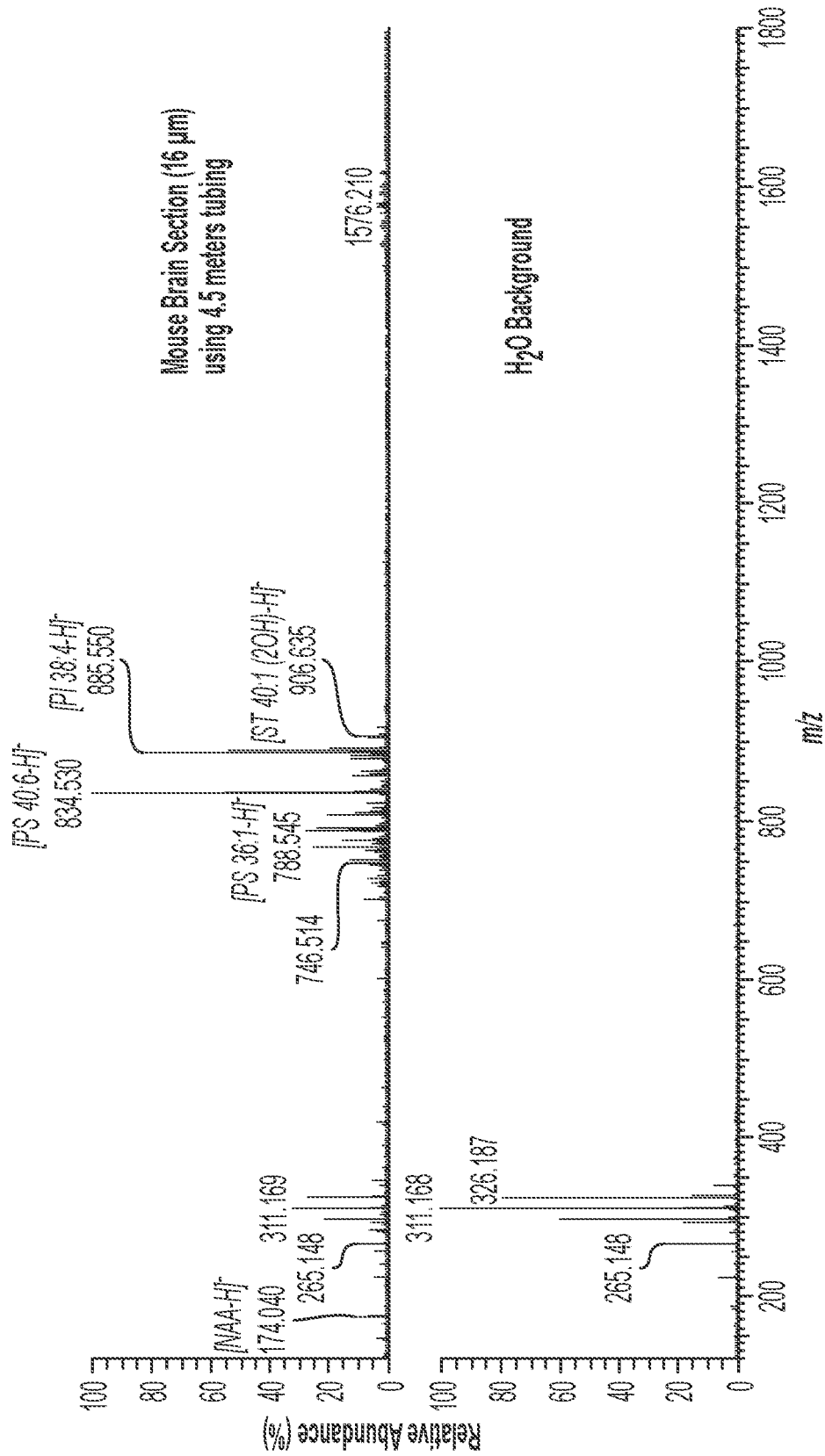
FIG. 16: Mass spectra generated from a 16 μm mouse brain section using 4.5 meter long tubing compared to the water background.
Figure 17:
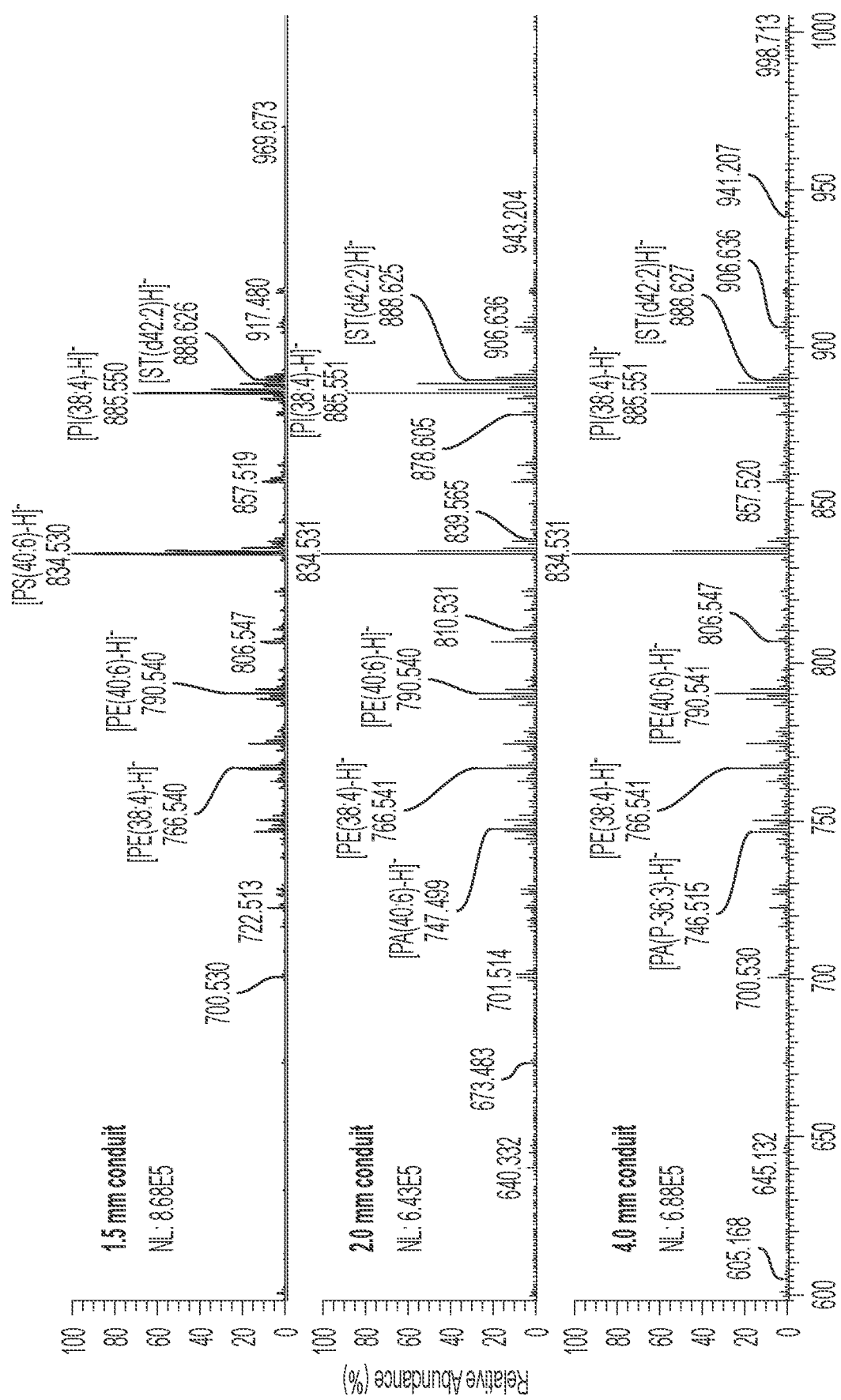
FIG. 17: Mass spectra generated with the minimally invasive mass spectrometry probe using Q Exactive Orbitrap Mass Spectrometer and conduits of 1.5-4.0 mm diameter.
Figure 19:
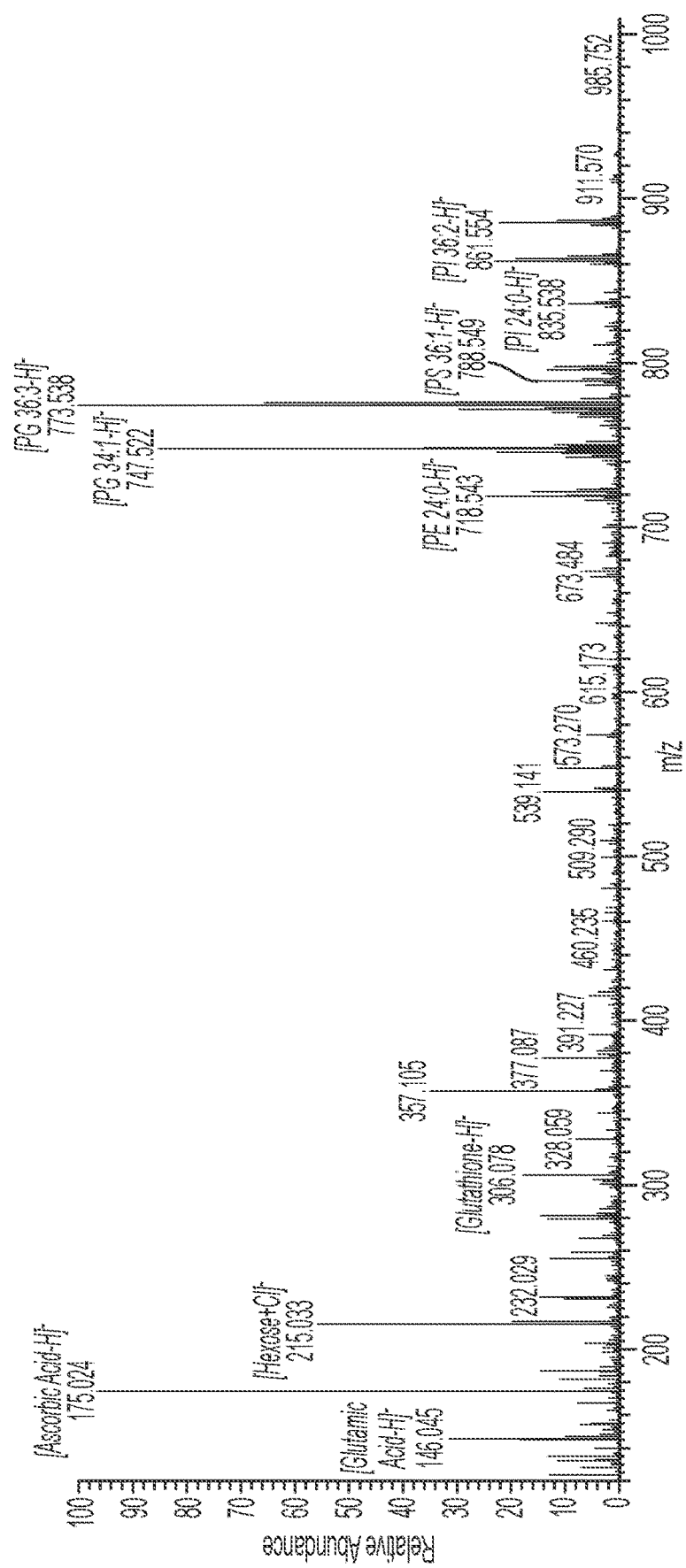
FIG. 19: Mass spectra of human lung tissue section from the minimally invasive mass spectrometry probe using Q Exactive Orbitrap Mass Spectrometer.

FIGS. 10-13 show the total ion chromatograms obtained from mouse brain sections during the total analysis period while using tubing lengths of 1.5 meters up to 4.5 meters. Rich molecular profiles were observed in all cases. At a tube length of 4.5 meters the molecular profile is easily established over the background signal of the water (FIG. 16). FIG. 17 shows total ion chromatograms obtained using conduit sizes from 1.5 mm to 4.0 mm. Again, rich molecular profiles were observed with each conduit size. To further demonstrate the utility of the minimally invasive probe for mass spectrometry, human lung tissue was analyzed (FIG. 19), and generated a robust molecular profile.

The molecular profiles generated by the minimally invasive mass spectrometry probe can also be used for tissue typing. A series of tissue samples were evaluated with the minimally invasive mass spectrometry probe and were able to be identified with an overall accuracy of 98.55% (Table 1).

TABLE 1

Tissue typing results

| TRUE | Thyroid | Lymph | Para-thyroid | Breast | Lung | Ovarian | Pancreas |
|---|---|---|---|---|---|---|---|
| Thyroid | 42 | 0 | 1 | 0 | 0 | 0 | 0 |
| Lymph | 0 | 26 | 0 | 0 | 0 | 0 | 0 |
| Para-thyroid | 0 | 1 | 62 | 0 | 0 | 0 | 0 |
| Breast | 0 | 0 | 0 | 29 | 0 | 0 | 0 |
| Lung | 0 | 0 | 0 | 0 | 47 | 0 | 0 |
| Ovarian | 0 | 1 | 0 | 1 | 0 | 41 | 0 |
| Pancreas | 0 | 0 | 0 | 0 | 0 | 0 | 24 |

The system was able to identify lymph, breast, and lung tissues with 100% accuracy, thyroid and parathyroid with between 97% and 99% accuracy, ovarian with 95.35% accuracy, and pancreas tissue with 83.33% accuracy. These tissue typing results were generated from selected features of the mass spectrometry profiles shown in Table 2.

TABLE 2

Selected features for tissue typing.

| | Thyroid | Lymph | Parathyroid | Breast | Lung | Ovarian | Pancreas |
|---|---|---|---|---|---|---|---|
| m/z | −0.25915 | −1.37199 | 0.833471 | −0.44036 | −0.34999 | 2.269018 | −0.68101 |
| 125.01 | 0 | 0 | 0 | 0 | 0 | 0.097137 | 0 |
| 130.06 | 0 | 0 | 0.008242 | 0 | 0 | 0 | 0 |
| 146.05 | 0 | 0 | −0.00177 | 0 | 0 | 0 | 0 |
| 147.69 | 0 | 0 | 0.28651 | 0 | 0 | 0 | 0 |
| 148.95 | 0 | 0 | 0 | 0 | 0 | 0.025703 | 0 |
| 183.96 | 0 | 0 | 0 | 0 | 0 | 0.014118 | 0 |
| 191.02 | 0 | 0 | 0 | 0 | 0 | −0.01003 | 0 |
| 194.99 | 0 | 0 | 0 | 0 | 0.00062 | 0 | 0 |
| 200.17 | 0 | −0.00053 | 0 | 0 | 0 | 0 | 0 |
| 205.46 | 0 | 0 | 0 | 0 | 0 | 0 | 0.260268 |
| 218.1 | 0 | 0 | −0.01171 | 0 | 0 | 0 | 0 |
| 239.17 | 0 | −0.02264 | 0 | 0 | 0 | 0 | 0 |
| 241.92 | 0 | 0 | 0 | 0 | 0 | 0.00716 | 0 |
| 243.97 | 0 | 0 | −0.01202 | 0 | 0 | 0 | 0 |
| 244.92 | 0 | 0 | 0.004177 | 0 | 0 | 0 | 0 |
| 250.96 | 0.064681 | 0 | 0 | 0 | 0 | 0 | 0 |
| 251.96 | 0 | 0 | 0 | 0 | 0 | 0.030521 | 0 |
| 252.85 | 0 | 0.00771 | 0 | 0 | 0 | 0 | 0 |
| 255.9 | 0 | 0 | 0 | 0 | 0 | 0.032836 | 0 |
| 256.23 | 0 | 0 | 0 | 0 | 0.009842 | 0 | 0 |
| 271 | 0 | 0 | −0.0484 | 0 | 0 | 0 | 0 |
| 271.19 | 0 | −0.00793 | 0 | 0 | 0 | 0 | 0 |
| 272.01 | 0 | 0 | 0.042591 | 0 | 0 | 0 | 0 |
| 273.08 | 0 | 0 | 0.015766 | 0 | 0 | 0 | 0 |
| 276.8 | 0.014438 | 0 | 0 | 0 | 0 | 0 | 0 |
| 279.24 | 0 | 0 | 0 | 0 | 0.011053 | 0 | 0 |
| 279.92 | 0 | 0 | 0 | 0 | −0.03074 | 0 | 0 |
| 287.01 | 0 | 0 | 0 | 0 | 0 | 0.026693 | 0 |
| 287.98 | 0 | 0 | 0.131242 | 0 | 0 | 0 | 0 |
| 291.01 | 0 | 0.081933 | 0 | 0 | 0 | 0 | 0 |
| 294.82 | 0 | 0 | −0.01746 | 0 | 0 | 0 | 0 |
| 296.09 | 0 | 0 | −0.01414 | 0 | 0 | 0 | 0 |
| 296.94 | 0 | 0 | 0 | 0 | 0 | 0 | 0.105634 |
| 306.07 | 0 | 0 | 0 | 0 | 0.016765 | 0 | 0 |
| 318.85 | 0 | 0 | 0 | 0 | 0 | 0.004345 | 0 |
| 323.91 | 0 | 0 | 0 | 0 | 0 | 0.025689 | 0 |
| 326.06 | 0 | 0 | 0.031889 | 0 | 0 | 0 | 0 |
| 332.27 | 0 | 0 | 0 | 0 | 0 | 0.064138 | 0 |
| 341.27 | 0 | 0 | 0 | 0.01519 | 0 | 0 | 0 |
| 344.97 | 0 | 0 | 0 | 0 | 0 | 0.066306 | 0 |
| 354.16 | 0 | 0 | 0 | 0 | 0 | −0.04315 | 0 |
| 357.84 | 0 | 0 | 0 | 0 | 0 | 0.011447 | 0 |
| 362.24 | 0 | 0 | −0.07847 | 0 | 0 | 0.000379 | 0 |
| 407.23 | 0 | 0 | 0 | 0 | 0 | −0.00779 | 0 |
| 428.03 | 0 | 0.089313 | 0 | 0 | 0 | 0 | 0 |
| 428.19 | 0 | 0 | 0 | 0 | 0 | −0.00888 | 0 |
| 436.28 | 0 | 0 | 0 | 0 | 0 | 0 | 0.006734 |
| 437.29 | 0 | 0 | 0 | 0 | 0 | 0 | 0.077554 |
| 444.08 | 0.151553 | 0 | 0 | 0 | 0 | 0 | 0 |
| 453.28 | 0 | 0 | 0 | 0 | 0 | −0.00176 | 0 |
| 455.8 | 0 | 0 | 0 | 0 | 0 | 0.01032 | 0 |
| 460.23 | 0 | 0 | 0 | 0 | 0 | −0.04105 | 0 |

TABLE 2-continued

Selected features for tissue typing.

|  | Thyroid | Lymph | Parathyroid | Breast | Lung | Ovarian | Pancreas |
|---|---|---|---|---|---|---|---|
| 462.3 | 0 | 0 | 0 | 0 | 0 | 0 | 0.08139 |
| 463.98 | 0 | 0 | 0.024299 | 0 | 0 | 0 | 0 |
| 465.3 | 0 | 0 | 0 | 0 | 0 | −0.03072 | 0 |
| 465.32 | 0 | 0 | 0 | 0 | 0 | 0 | 0.012348 |
| 476.21 | 0 | 0 | −0.02093 | 0 | 0 | 0 | 0 |
| 485.2 | 0 | 0 | 0 | 0 | 0 | 0.032981 | 0 |
| 519.32 | 0 | 0 | 0 | 0.181706 | 0 | 0 | 0 |
| 524.3 | 0 | 0 | 0 | 0 | 0 | 0 | 0.0418 |
| 530.26 | 0 | 0 | 0.011799 | 0 | 0 | 0 | 0 |
| 535.13 | 0 | 0 | 0 | 0 | 0 | 0.041376 | 0 |
| 565.05 | 0 | 0 | 0.076194 | 0 | 0 | 0 | 0 |
| 578.27 | 0 | 0.067343 | 0 | 0 | 0 | 0 | 0 |
| 616.17 | 0 | 0 | 0 | 0 | 0 | −0.03131 | 0 |
| 637.33 | 0.100992 | 0 | 0 | 0 | 0 | 0 | 0 |
| 655.51 | 0 | 0 | 0 | 0 | 0 | 0 | 0.088267 |
| 688.51 | 0 | 0 | 0 | 0.064253 | 0 | 0 | 0 |
| 690.51 | 0 | 0 | 0 | 0 | 0.044558 | 0 | 0 |
| 701.53 | 0 | 0 | 0 | 0 | 0 | −0.00473 | 0 |
| 714.51 | 0 | 0 | 0 | 0 | 0 | −0.02904 | 0 |
| 715.54 | 0 | 0 | 0 | 0.286059 | 0 | 0 | 0 |
| 717.53 | 0 | 0 | 0.032346 | 0 | 0 | 0 | 0 |
| 718.54 | 0 | 0 | 0 | 0 | 0.107471 | 0 | 0 |
| 719.49 | 0 | 0 | 0 | 0 | 0.166554 | 0 | 0 |
| 721.5 | 0 | 0 | 0 | 0 | 0.019482 | 0 | 0 |
| 724.99 | 0 | 0 | 0.012692 | 0 | 0 | 0 | 0 |
| 725.49 | 0 | 0 | 0.061029 | 0 | 0 | 0 | 0 |
| 726.5 | 0 | 0 | 0.022406 | 0 | 0 | 0 | 0 |
| 729.37 | 0 | 0.077857 | 0 | 0 | 0 | 0 | 0 |
| 741.53 | 0 | 0 | 0.04295 | 0 | 0 | 0 | 0 |
| 743.57 | 0 | 0 | 0 | 0.023627 | 0 | 0 | 0 |
| 747.52 | 0 | 0 | 0 | 0 | 0 | −0.0096 | 0 |
| 748.52 | 0 | 0 | 0 | 0 | 0.140912 | 0 | 0 |
| 752.56 | 0 | 0 | 0 | 0 | 0.022913 | 0 | 0 |
| 758.4 | 0.0479 | 0 | 0 | 0 | 0 | 0 | 0 |
| 761.4 | 0.025123 | 0 | 0 | 0 | 0 | 0 | 0 |
| 764.52 | 0 | 0 | 0.003296 | 0 | 0 | 0 | 0 |
| 768.55 | 0 | 0 | 0.002224 | 0 | 0 | 0 | 0 |
| 769.5 | 0 | 0 | 0 | 0 | 0 | −0.00431 | 0 |
| 769.51 | 0 | 0 | 0 | 0 | 0.004727 | 0 | 0 |
| 770.53 | 0 | 0 | 0 | 0 | 0.08501 | 0 | 0 |
| 771.52 | 0 | 0 | 0 | 0 | 0 | −0.03674 | 0 |
| 775.55 | 0 | 0 | 0 | 0 | 0 | −0.02396 | 0 |
| 776.55 | 0 | 0 | 0 | 0 | 0.121705 | 0 | 0 |
| 793.56 | 0 | 0.012003 | 0 | 0 | 0 | 0 | 0 |
| 795.52 | 0 | 0 | 0 | 0 | 0.039051 | 0 | 0 |
| 796.52 | 0 | 0 | 0 | 0 | 0.024792 | 0 | 0 |
| 809.52 | 0 | 0 | 0.063972 | 0 | 0 | 0 | 0 |
| 811.53 | 0 | 0.047294 | 0 | 0 | 0 | 0 | 0 |
| 812.55 | 0 | 0.087882 | 0 | 0 | 0 | 0 | 0 |
| 813.55 | 0 | 0.031647 | 0 | 0 | 0 | 0 | 0 |
| 822.47 | 0.062048 | 0 | 0 | 0 | 0 | 0 | 0 |
| 823.48 | 0.215822 | 0 | 0 | 0 | 0 | 0 | 0 |
| 833.52 | 0 | −0.0026 | 0 | 0 | 0 | 0 | 0 |
| 835.54 | 0 | −0.00055 | 0 | 0 | 0 | 0 | 0 |
| 836.55 | 0 | 0.311816 | 0 | 0 | 0 | 0 | 0 |
| 838.56 | 0 | 0.020823 | 0 | 0 | 0 | 0 | 0 |
| 860.54 | 0 | 0 | 0.004644 | 0 | 0 | 0 | 0 |
| 861.55 | 0 | 0 | 0 | 0 | 0 | −0.02476 | 0 |
| 991.29 | 0 | 0.001467 | 0 | 0 | 0 | 0 | 0 |
| 991.69 | 0 | 0.069562 | 0 | 0 | 0 | 0 | 0 |
| 1305.95 | 0 | 0 | 0 | 0 | 0 | 0.058809 | 0 |
| 1448.97 | 0 | 0 | 0.002613 | 0 | 0 | 0 | 0 |

Similarly to the differentiation of tissue types, the minimally invasive mass spectrometry probe can be used to differentiate between normal and cancerous tissues. The system predicted normal tissues with greater than 89% accuracy, and cancer tissues with greater than 91% accuracy as seen in Table 3.

TABLE 3

Cancer tissue prediction results

|  |  | Predicted | |
|---|---|---|---|
|  |  | Normal | Cancer |
| True | Normal | 247 | 28 |
|  | Cancer | 12 | 129 |

These tissues were predicted based on the selected features shown in Table 4.

TABLE 4

Selected features used for the prediction of cancer tissues.

| m/z | Cancer | MaxIntensityNorm | MinIntensityNorm | MaxIntensity | MinIntensity |
|---|---|---|---|---|---|
|  | −0.1200838 | 0.00000000 | 0 | 0.0 | 0 |
| 124.01 | −40.9603959 | 0.07309089 | 0 | 1910468.9 | 0 |
| 146.05 | −25.4909642 | 0.08721183 | 0 | 4249182.8 | 0 |
| 154.06 | −1.7548952 | 0.27268945 | 0 | 1028115.5 | 0 |
| 165.02 | 42.8950874 | 0.02168110 | 0 | 189918.4 | 0 |
| 174.04 | 114.2977347 | 0.01893967 | 0 | 703388.7 | 0 |
| 175.02 | −27.1843207 | 0.21139870 | 0 | 6752479.6 | 0 |
| 175.03 | −24.4596324 | 0.12211639 | 0 | 2175467.9 | 0 |
| 187.04 | −60.8607370 | 0.22046140 | 0 | 5731647.5 | 0 |
| 201.04 | 118.9618023 | 0.08163593 | 0 | 1262331.3 | 0 |
| 214.05 | −128.8755917 | 0.03867785 | 0 | 773249.9 | 0 |
| 215.03 | −31.7356346 | 0.09055005 | 0 | 3274645.3 | 0 |
| 221.01 | 138.9164198 | 0.01083151 | 0 | 568690.6 | 0 |
| 241.04 | −74.5285436 | 0.01626196 | 0 | 3302753.8 | 0 |
| 246.95 | −2.9550154 | 0.05776215 | 0 | 1111366.1 | 0 |
| 267.07 | 4.3468095 | 0.03979236 | 0 | 4039159.9 | 0 |
| 268.8 | −51.7317355 | 0.04524576 | 0 | 1488145.8 | 0 |
| 271 | −3.2679671 | 0.06004618 | 0 | 492594.7 | 0 |
| 283.27 | −55.5183712 | 0.14933261 | 0 | 2355024.1 | 0 |
| 296.94 | 7.5951233 | 0.22379688 | 0 | 2429905.2 | 0 |
| 313.16 | −3.7134875 | 0.17606736 | 0 | 7786035.2 | 0 |
| 328.06 | 71.2579706 | 0.04428292 | 0 | 957525.7 | 0 |
| 332.9 | 23.4374773 | 0.03396153 | 0 | 1214185.0 | 0 |
| 341.27 | −1.6023939 | 0.28304768 | 0 | 6590254.4 | 0 |
| 345.16 | −50.1650411 | 0.04368856 | 0 | 1696500.0 | 0 |
| 346.05 | 83.1031168 | 0.01781918 | 0 | 628038.1 | 0 |
| 353.16 | 23.4132756 | 0.06995437 | 0 | 2172310.7 | 0 |
| 377.09 | −9.9688497 | 0.10964367 | 0 | 1100627.9 | 0 |
| 559.47 | −2.7064435 | 0.05334380 | 0 | 49840406.6 | 0 |
| 572.48 | 83.3837979 | 0.01727858 | 0 | 1439590.6 | 0 |
| 585.49 | −20.0678254 | 0.09010271 | 0 | 86114572.9 | 0 |
| 615.17 | −115.9821356 | 0.03578691 | 0 | 2801168.1 | 0 |
| 722.51 | 66.9597188 | 0.04599428 | 0 | 13448313.9 | 0 |
| 742.54 | 89.8907769 | 0.04732031 | 0 | 8284542.5 | 0 |
| 744.55 | 64.7272067 | 0.02038387 | 0 | 905261.7 | 0 |
| 748.52 | −39.0756981 | 0.04027318 | 0 | 1870669.2 | 0 |
| 766.54 | −23.4133796 | 0.05266494 | 0 | 4504433.6 | 0 |
| 773.53 | −60.0910994 | 0.09127090 | 0 | 3784388.4 | 0 |
| 788.54 | 44.1054014 | 0.04591038 | 0 | 1660366.4 | 0 |
| 788.55 | −1.4204710 | 0.03125159 | 0 | 4032842.0 | 0 |
| 822.47 | −19.2490565 | 0.05601076 | 0 | 738427.0 | 0 |
| 823.48 | −66.6013083 | 0.02864992 | 0 | 320932.5 | 0 |
| 861.55 | −135.4621348 | 0.05829841 | 0 | 9614626.2 | 0 |
| 885.55 | 25.0244403 | 0.12046562 | 0 | 9712708.6 | 0 |
| 888.57 | 90.5815624 | 0.02339633 | 0 | 1145858.3 | 0 |

To evaluate the system performance, consecutive analysis was conducted on the same tissue section, and on different tissue sections to demonstrate that the system is highly reproducible within samples and across different samples.

Materials and Methods

Mass Spectrometer. Q Exactive Hybrid Quadrupole-Orbitrap mass spectrometer (Thermo Scientific, San Jose, CA) was used. Full-scan was carried out at the range of m/z 500-1800, and the other mass spectrometric parameters were listed as follows: resolving power 140,000, micro scan 2, maximum injection time 300 ms, capillary temperature 350° C. and S-lens RF level 100.

Biological Tissues. Wild-type mouse brains were purchased from Bioreclamation IVT. 62 frozen human tissue specimens including breast, thyroid, lymph node, ovarian, and kidney were obtained from Cooperative Human Tissue Network and Baylor College Tissue Bank. Samples were stored in a −80° C. freezer. Tissue slides were sectioned at 16 μm using a CryoStar™ NX50 cryostat. Frozen tissue specimen were thawed under room temperature before use.

Statistical Analysis. IBM SPSS Statistics 22.0 (IBM Corporation, Armonk, NY, USA) was used to perform principal component analysis (PCA) to reveal patterns in the data. The analysis was performed directly using the raw data. The 10 peaks of the top relative intensities in the m/z range of 700-900 were used for PCA. Typically, the first three components, which all encompassed more than 85% of the total variance, are used in the present results.

Example 3

System Automation for Handheld and Laparoscopic Use

Because all the materials (PDMS and PTFE) and solvent (only water) used in the minimally invasive probe design are biologically compatible, the system has a high potential to be used in laparoscopic and endoscopic surgeries for real-time analysis. More than that, due to the small dimension of the device, it can be integrated to a robotic surgical system, such as the Da Vinci surgical system, through an accessory port or one of its robotic arms. Several regions of the human body cavity can be quickly sampled during surgery with or without wash/flush steps in between each analysis, and analyzed by using a database of molecular signatures and machine learning algorithms. Therefore, the diagnosing results may be provided in real time for each sampled region. This system can be broadly used in a wide variety of oncological and other surgical interventions (such as endometriosis) for which real-time characterization and diagnosis of tissues are needed.

Example 4

System with Pneumatic Applicator

Figure 21:
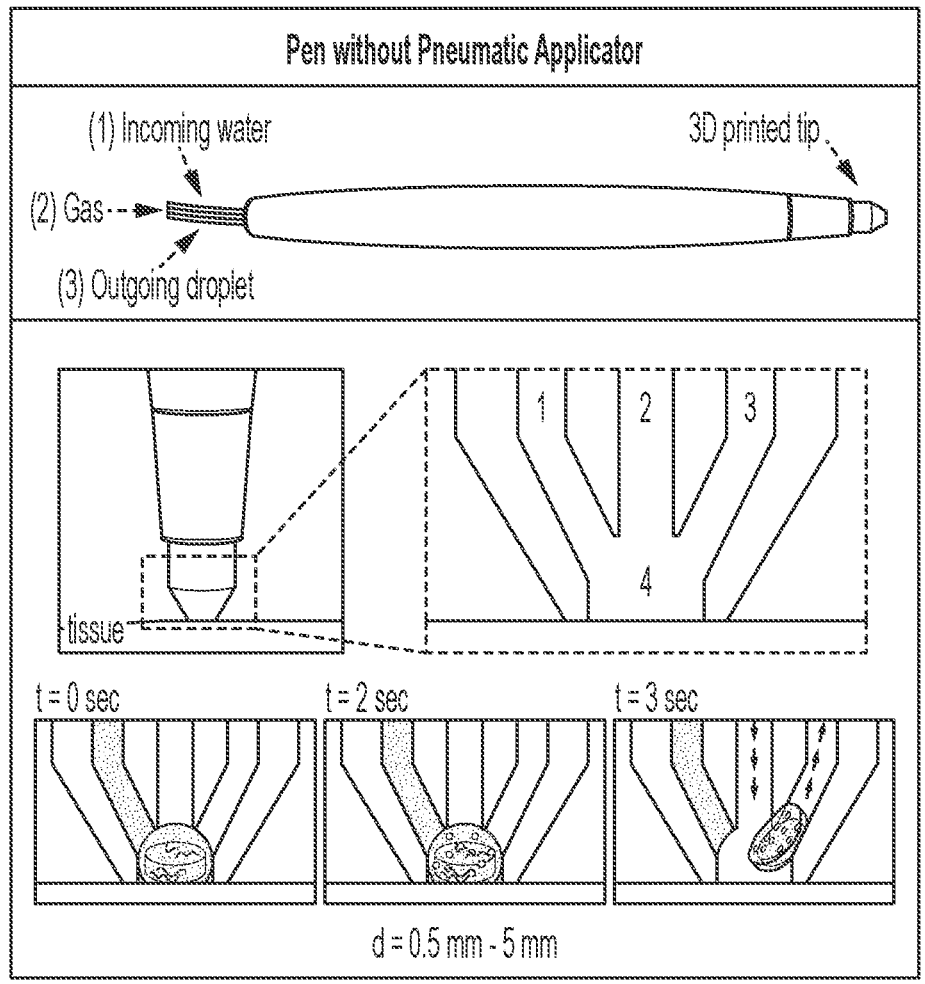
FIG. 21: Representative schematic with of a device without a pneumatic applicator that can provide a vacuum pressure to a surface in contact with the device.
Figure 22:
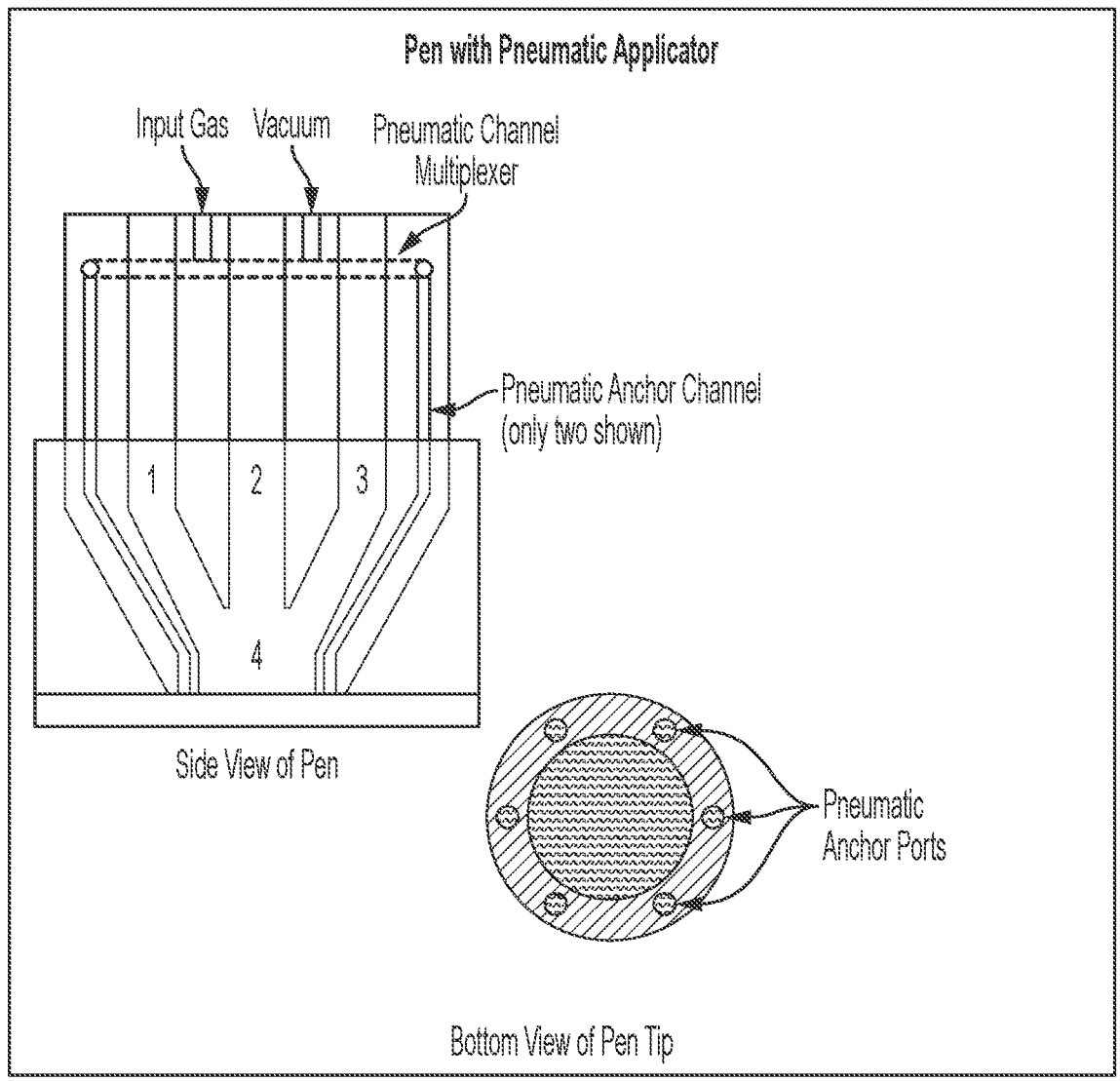
FIG. 22: Representative schematic with of a device with a pneumatic applicator that can provide a vacuum pressure to a surface in contact with the device.
Figure 23:
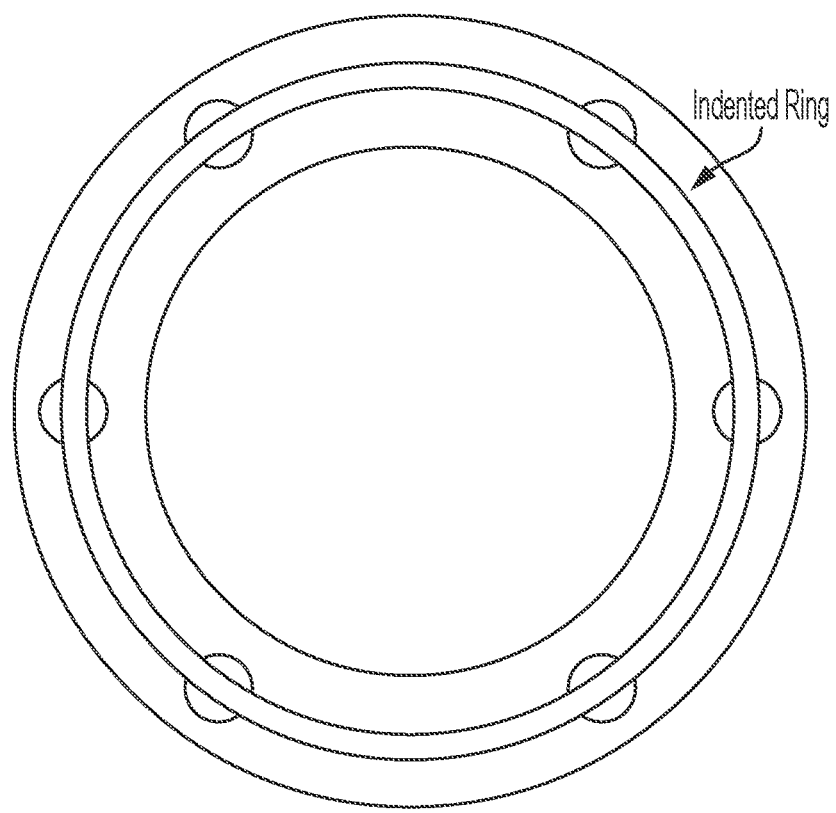
FIG. 23: End view of a device with the vacuum ports that includes an additional indented ring that extends around the perimeter of the device and provides vacuum pressure to the surface in contact with the device.

Referring now to FIGS. 21-23, an embodiment is shown with a pneumatic applicator that can provide a vacuum pressure to a surface in contact with the device. FIG. 21 shows a side view and section views of a device without the pneumatic applicator for comparison. FIG. 22 illustrates section and end view of a device with pneumatic anchor or vacuum ports configured to provide suction to the surface in contact with the device. The vacuum ports are in fluid communication with pneumatic channels and a pneumatic channel multiplexer (shown in the section view) that provide a vacuum pressure to the ports via a vacuum source. In the embodiment shown, the pneumatic channel multiplexer is a circumferential ring extending around the device and in fluid communication with the pneumatic channels. In the embodiment shown in FIG. 22 the ports are formed by the ends of the channels that extend from the circumferential ring multiplexer to the surface at the end of the device configured to contact tissue. In other embodiments, the vacuum ports may comprise additional features, as shown and discussed below.

During operation, the device (e.g. a MasSpec Pen) with pneumatic application contains anchor ports that (when in contact with a tissue surface) apply a vacuum pressure to anchor the tissue to the pen tip. When the device is not in contact with tissue, a small positive gauge pressure may be applied with a clean gas (e.g, nitrogen). Transitions between vacuum and positive pressure gas flow can be initiated either by a human operator or autonomously utilizing a contact sensor. One purpose of the small positive gauge pressure is to maintain open pneumatic anchor channels when the Pen is not in contact with the tissue surface. The flow of clean gas will keep the pneumatic anchor channels free of fluids or debris that may enter while the pen is in contact with a tissue surface. In certain scenarios (e.g, one-time use), the pneumatic applicator can be operated without the small positive gauge pressure and utilize the vacuum port only.

FIG. 23 illustrates an end view of a device where the vacuum ports include an additional indented ring that extends around the perimeter of the device and provides vacuum pressure to the surface in contact with the device. The indented ring is in fluid communication with the end of the channels that extend from the circumferential ring multiplexer so that a greater area is created for the vacuum ports. This can allow a greater vacuum force to be generated when the device is applied to the tissue.

Embodiments with vacuum pressure application may be operated in a number of different ways. For example, in one aspect, human operation with a foot pedal can be used to initiate vacuum. The foot pedal can be configured to operate in a two state mode where a partial depression activates the vacuum while a full depression initiates a MasSpec Pen measurement. In another aspect, autonomous operation with a contact sensor can be used to either initiate vacuum and/or to provide small positive pressure flow. In this mode of operation, the use of a threshold sensor detects the contact pressure between the device and the tissue surface. When the contact pressure sensor transitions from below to above the threshold level, the vacuum is activated. When the contact pressure drops from above to below the threshold pressure, the small positive pressure is applied. Contact pressure sensors known in the art may include snap switches, springs, PVDF films, etc. In certain aspects, the pneumatic ports may be operated by a vacuum pressure only. In such examples, a trap can be employed to capture tissue fluids and debris to maintain a vacuum pressure.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An apparatus comprising: a cassette comprising a plurality of sample acquisition probes; a sample processing instrument configured to receive a sample;
   a first plurality of conduits; a first chamber comprising a solvent; and
   a gas supply; wherein: the cassette is coupled to the sample processing instrument; a first sample acquisition probe is in fluid communication with the sample processing instrument when the cassette is in a first orientation;
   a second sample acquisition probe is in fluid communication with the sample processing instrument when the cassette is in a second orientation; and the cassette can be is configured to be moved from the first orientation to the second orientation while the cassette is coupled to the sample processing instrument;
   wherein: each sample acquisition probe is in fluid communication with an individual conduit of the first plurality of conduits; and each individual conduit of the first plurality of conduits is configured to place a single sample acquisition probe in fluid communication with the sample processing instrument when the cassette is oriented to align the individual conduit with the sample processing instrument; and wherein each sample acquisition probe in the plurality of sample acquisition probes comprises a reservoir, a first conduit, a second conduit, a third conduit, and a funnel-shaped chamber, wherein: the first conduit is in fluid communication with the first chamber; the second conduit is in fluid communication with the gas supply; the third conduit is in fluid communication with the sample processing instrument; the first conduit, the second conduit, and the third conduit each comprises a respective terminus at the reservoir, such that each of the first conduit, the second conduit, and the third conduit are each in fluid in communication with the reservoir; and the second conduit further comprising the funnel-shaped chamber, wherein the funnel-shaped chamber of the second conduit extending extends from a smaller end to a larger end, the larger end of the funnel-shaped chamber being proximal to the reservoir, and the smaller end of the funnel-shaped chamber being distal from the reservoir, such that the second conduit is in fluid communication with the reservoir via the funnel-shaped chamber of the second conduit.

2. The apparatus of claim 1 wherein the sample processing instrument is a mass spectrometer.

3. The apparatus of claim 1 wherein the cassette rotates from the first orientation to the second orientation.

4. The apparatus of claim 1 wherein the cassette moves linearly from the first orientation to the second orientation.

5. The apparatus of claim 1, wherein the gas supply is the ambient air and the apparatus comprises a valve or conduit that is open to the ambient air.

6. The apparatus of claim 1, wherein the gas supply is a pressurized gas supply, and wherein the pressurized gas supply provides a gas to the probe at a pressure less than 100 psig.

7. The apparatus of claim 1, wherein the solvent comprises water, ethanol, or a combination thereof.

8. The apparatus of claim 1, wherein the solvent comprises an aqueous mixture including from 1 to 25% ethanol.

9. The apparatus of claim 1, further comprising:
a second chamber comprising a cleaning fluid; and
a conduit in fluid communication with the second chamber and the plurality of sample acquisition probes.

10. The apparatus of claim 1 wherein the sample acquisition probe is, or is comprised in, a cannula of a surgical instrument.

11. The apparatus of claim 1, wherein each conduit between each sample acquisition probe and the sample processing instrument comprises a valve configured to restrict flow through the conduit.

12. The apparatus of claim 1, wherein each sample acquisition probe of the plurality of sample acquisition probes comprises a distal probe end, and the distal probe end comprises a shutter configured to be closed to prevent fluid communication outside of the sample acquisition probe.

13. The apparatus of claim 1, wherein each sample acquisition probe is configured to contact tissue and obtain the sample from the tissue.

14. The apparatus of claim 13, wherein each sample acquisition probe is configured to:
apply a fixed volume of the solvent to a tissue site; and
collect the applied solvent to obtain the sample.

* * * * *